US011220680B2

(12) United States Patent
Chang et al.

(10) Patent No.: US 11,220,680 B2
(45) Date of Patent: Jan. 11, 2022

(54) POLYPEPTIDE FOR TREATING PATHOLOGICAL BLOOD CLOTS

(71) Applicant: Immunwork Inc., Taipei (TW)

(72) Inventors: Tse-Wen Chang, Taipei (TW); Hsing-Mao Chu, Taipei (TW); Wei-Ting Tian, Taipei (TW); Ting-Wei Chang, Taipei (TW); Ming-Yu Hsieh, Taipei (TW)

(73) Assignee: IMMUNWORK INC., Taipei (TW)

( * ) Notice: Subject to any disclaimer, the term of this patent is extended or adjusted under 35 U.S.C. 154(b) by 75 days.

(21) Appl. No.: 16/691,578

(22) Filed: Nov. 21, 2019

(65) Prior Publication Data

US 2020/0157519 A1 May 21, 2020

Related U.S. Application Data

(60) Provisional application No. 62/770,188, filed on Nov. 21, 2018.

(51) Int. Cl.
*C07K 16/18* (2006.01)
*C07K 16/36* (2006.01)
*C12N 9/72* (2006.01)

(52) U.S. Cl.
CPC ............ *C12N 9/6459* (2013.01); *C07K 16/18* (2013.01); *C07K 2317/24* (2013.01); *C07K 2317/569* (2013.01); *C07K 2317/622* (2013.01); *C12Y 304/21068* (2013.01)

(58) Field of Classification Search
None
See application file for complete search history.

(56) References Cited

U.S. PATENT DOCUMENTS 5,811,265 A * 9/1998 Quertermous ............................... C12Y 304/21073 435/69.3
2017/0056518 A1 * 3/2017 Chang .................... A61K 47/64

OTHER PUBLICATIONS

Kussie et al., A single engineered amino acid substitution changes antibody fine specificity. J Immunol. Jan. 1, 1994;152(1):146-52. (Year: 1994).*
Edwards et al., The remarkable flexibility of the human antibody repertoire; isolation of over one thousand different antibodies to a single protein, BLyS. J Mol Biol. Nov. 14, 2003;334(1):103-18. (Year: 2003).*
Chen et al., Enhancement and destruction of antibody function by somatic mutation: unequal occurrence is controlled by V gene combinatorial associations. EMBO J. Jun. 15, 1995;14(12):2784-94. (Year: 1995).*

* cited by examiner

*Primary Examiner* — Aurora M Fontainhas

(57) ABSTRACT

The present disclosure provides a polypeptide including an anti-fibrin antibody and a serine protease moiety of human tissue plasminogen activator. Methods for treating thrombosis in a subject in need of such treatment using such polypeptide are also disclosed.

15 Claims, 17 Drawing Sheets
(1 of 17 Drawing Sheet(s) Filed in Color)
Specification includes a Sequence Listing.

POLYPEPTIDE FOR TREATING PATHOLOGICAL BLOOD CLOTS

CROSS-REFERENCE TO RELATED APPLICATION

This application relates to and claims the benefit of U.S. Provisional Application No. 62/770,188, filed Nov. 21, 2018, the content of the above-mentioned application is incorporated herein by reference in its entirety.

BACKGROUND OF THE INVENTION

1. Field of the Invention

The present disclosure relates to the field of polypeptides; more particularly, to a polypeptide comprises an anti-fibrin antibody and a serine protease moiety of human tissue plasminogen activator (hu-tPA), and its use in treating thrombosis.

2. Description of the Related Art

Blood clotting (or coagulation) is a complex process by which the blood forms blood. Coagulation involves a cascade of protease-catalyzed events, which amplify in sequence. Toward the later steps, Factor Xa cleaves prothrombin to generate thrombin, and thrombin in turns cleaves fibrinogen to fibrin, which in combination with platelets forms the meshwork of a clot. The dissolution of the blood clot involves plasmin, which is generated from plasminogen via one of several enzymes, including tissue plasminogen activator.

Thrombosis is a disorder of coagulation, in which the blood clot (or thrombus) blocks the blood vessel and hence obstructs the blood flow in the affected area. Patients suffering from various complications (e.g., those resulted from cardiovascular, endocrine or other bodily regulatory conditions, surgery, the use of medicine, among the others) have the tendency to develop such pathological blood clots. These clots may cause hemorrhagic strokes, head trauma, myocardial infarction, pulmonary embolism, or deep vein thrombosis, which often lead to serious, life-threatening clinical conditions.

There are two main aspects of pharmaceutical needs in dealing with such pathological problems of blood clotting: one aspect is to prevent or inhibit pathological blood clots to form or to grow in size once a nucleus of clot is formed, and the other aspect is to dissolve already-formed pathological clots timely. In both aspects, there are batteries of pharmaceutical products available clinically.

A large number of indirect inhibitors of Factor Xa have been developed and used. For many decades, the inhibitors are primarily heparin, which is a mixture of naturally occurring polysaccharides of glycosaminoglycan of varying molecular weights from 5 to 30 kDa, low-molecular-weight heparin, and heparinoid compounds. Those substances bind to heparin-binding proteins, including anti-thrombin, thus potentiating those substances to inhibit Factor Xa, thereby inhibiting the clot formation. Tissue factor pathway inhibitor (TFPI), a single-chain serum protein of 34 to 40 kDa depending on the degree of proteolysis, can inhibit Factor Xa. However, it is not produced using the recombinant DNA technology as a therapeutic.

A number of direct inhibitors of thrombin have also been developed and used clinically. Naturally recovered hirudin from medical leeches and recombinant hirudin, which bind to thrombin, were used for many years before they were discontinued because of the introduction of other better medicines.

More recently, several small molecules that are direct inhibitors of Factor Xa or thrombin have been developed and approved for clinical uses in preventing coagulation in several clinical indications. In one set of clinical applications, these small molecules are direct inhibitors of Factor Xa, such as apixaban, edoxaban, or rivaroxaban. In another set of applications, these small molecules are direct inhibitors of thrombin, such as argatroban or dabigatran. Ximelagatran, a direct thrombin inhibitor, has favorable kinetics and may be administered in very small doses; however, it has been withdrawn from the market due to hepatoxicity problems.

The development of several forms of recombinant human tissue plasminogen activator (tPA), including alteplase, reteplase, tenecteplase, and lanoteplase, has solved a significant part of the thrombosis problems. However, the use of tPA in many cases either is not sufficient to dissolve the clots or causes serious internal bleeding, or both.

The molecular structure of an intact tPA is complex for the intact tPA comprises several structural domains with discrete functions or activities, although not all of these domains are required for a thrombolytic product suitable for use in dissolving blood clots. A full-length tPA molecule (alteplase) with 527 amino acid residues contains, (i) a fibronectin finger domain that binds to fibrin, (2) an epidermal growth factor domain that binds to hepatocytes and facilitates tPA's clearance, (3) a Kringle 1 domain that binds to hepatic endothelial cells and facilitates tPA' clearance, (4) a Kringle 2 domain that binds to fibrin and activates the serine protease, and (5) a protease domain that cleaves plasminogen and is inhibited by plasminogen activator inhibitor type 1 (PAI-1). Alteplase, tenecteplase, and lanoteplase are produced in mammalian cells, CHO cells, and reteplase is produced in bacteria.

Reteplase, which is 355-residue in length, does not contain the fibronectin finger, epidermal growth factor domain, and Kringle 1 domain. Reteplase is produced in bacteria, and therefore it does not contain the posttranslational carbohydrate modification. While reteplase has a lower affinity for fibrin and its protease is not activated to the extent as in alteplase, reteplase has a plasma half-life of 14-18 minutes; in contrast, the half-life period of alteplase only lasts 3-4 minutes in plasma. Reteplase is administered to patients in boli, while alteplase is administered in a bolus followed by an infusion.

Tenecteplase has the entire length of 527 amino acid residues of alteplase but has mutations at three sites. Threonine at 103 is replaced by asparagine to allow glycosylation modification, and asparagine at 117 is replaced by glutamine to eliminate glycosylation. These mutations inhibit the clearance of the molecule by liver cells. In addition, the four residues at 296-299 (i.e., lysine-histidine-arginine-arginine) are replaced by four alanine residues, thus increasing the resistance to PAI-1 by 80 times. Tenecteplase has a plasma half-life of 18 minutes.

In lanoteplase, the fibronectin finger and the epidermal growth factor domain are deleted and the asparagine at 117 is replaced by glutamine. The plasma half-life of lanoteplase is increased to 45 minutes, which improves administration procedures.

The clinical studies comparing the several forms of recombinant tPA are also very active. In various clinical trials, the overall therapeutic efficacies of the four forms of tPA are about equal, and each seems to fit better than others do in particular clinical conditions. From the wealth of published literature on tPA and its variants and their medical uses, it is apparent that the various properties of tPA, including the affinity in binding to fibrin, its half-life, the susceptibility to breakdown by liver cells, and the resistance to plasminogen activator inhibitor all play part in the desired properties of the tPA for a particular clinical condition.

In view of the foregoing, there exists a need in the related art for still better products for treating pathological or obstructive blood clots.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

In a first aspect, the present disclosure is directed to an antibody specific for fibrin. According to various embodiments of the present disclosure, the anti-fibrin antibody is specific for the human or mouse fibrin. Moreover, the present anti-fibrin antibody preferentially binds with polymerized, insoluble fibrin over the soluble fibrinogen. According to some embodiments of the present invention, the anti-fibrin antibody binds to human fibrin with an affinity 10 times better than to human fibrinogen.

In some optional embodiments, the anti-fibrin antibody comprises a light-chain variable domain having the amino acid sequence of SEQ ID NOs: 1, 17, 19, or 21, and a heavy-chain variable domain having the amino acid sequence of SEQ ID NOs: 2, 18, 20, or 22. For example, the anti-fibrin antibody may be an scFv having the amino acid sequence of SEQ ID NO. 3 or 5.

According to certain embodiments of the present disclosure, the anti-fibrin antibody comprises six complementarity-determining regions (CDRs) respectively having the amino acid sequences corresponding to residues 30 to 32 of SEQ ID NO: 1 (CDR-L1), residues 49 to 54 of SEQ ID NO: 1 (CDR-L2), residues 91 to 96 of SEQ ID NO: 1 (CDR-L3), residues 30 to 33 of SEQ ID NO: 2 (CDR-H1), residues 50 to 59 of SEQ ID NO: 2 (CDR-H2), and residues 98 to 106 of SEQ ID NO:2 (CDR-H3).

According to various embodiments of the present disclosure, the anti-fibrin antibody is a single-chain variable fragment (scFv) or single-domain antibody (sdAb).

In other optional embodiments, the light-chain variable domain and the heavy-chain variable domain is linked with a hydrophilic linker having the sequence of SEQ ID NO: 16.

In another aspect, the present disclosure is directed to a polypeptide that comprises the anti-fibrin antibody according to the above-mentioned aspect/embodiments of the present disclosure. As could be appreciated, methods for treating thrombosis using such polypeptides also fall within the aspect of the present disclosure.

According to embodiments of the present disclosure, the polypeptide comprises an anti-fibrin antibody and a serine protease moiety of human plasminogen activator (hu-tPA), wherein the anti-fibrin antibody binds to human fibrin with an affinity 10 times better than to human fibrinogen. Alternatively, or additionally, the polypeptide binds to human fibrin better than the hu-tPA does. Still alternatively or additionally, the polypeptide has a longer serum half-life in an animal than reteplase does.

Particular, the serine protease moiety of tPA is linked to the N- or C-terminus of the anti-fibrin antibody, directly or indirectly with a linking sequence therebetween.

According to optional embodiments of the present disclosure, the serine protease moiety of hu-tPA is reteplase.

In some embodiments, the anti-fibrin antibody is of human origin or humanized.

According to certain embodiments of the present disclosure, the polypeptide has the amino acid sequence of SEQ ID NO. 11 or 12, or 14.

Many of the attendant features and advantages of the present disclosure will becomes better understood with reference to the following detailed description considered in connection with the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present description will be better understood from the following detailed description read in light of the accompanying drawings, where.

Figure 1A:
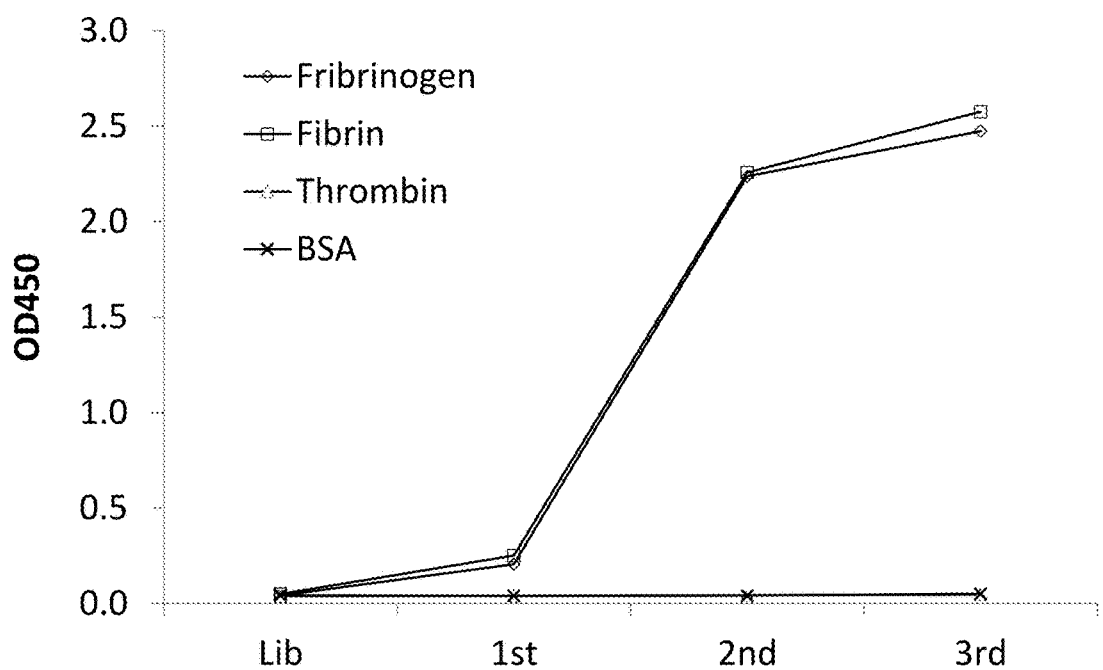
FIG. 1A shows the result of phage titer analysis of phage-displayed scFvs specific for human fibrin.

In accordance with common practice, the various described features/elements are not drawn to scale but instead are drawn to best illustrate specific features/elements relevant to the present invention. Also, like reference numerals and designations in the various drawings are used to indicate like elements/parts, where possible.

DESCRIPTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

For convenience, certain terms employed in the specification, examples and appended claims are collected here. Unless otherwise defined herein, scientific and technical terminologies employed in the present disclosure shall have the meanings that are commonly understood and used by one of ordinary skill in the art.

Unless otherwise required by context, it will be understood that singular terms shall include plural forms of the same and plural terms shall include the singular. Specifically, as used herein and in the claims, the singular forms "a" and "an" include the plural reference unless the context clearly indicated otherwise. Also, as used herein and in the claims, the terms "at least one" and "one or more" have the same meaning and include one, two, three, or more. Furthermore, the phrases "at least one of A, B, and C", "at least one of A, B, or C" and "at least one of A, B and/or C," as use throughout this specification and the appended claims, are intended to cover A alone, B alone, C alone, A and B together, B and C together, A and C together, as well as A, B, and C together.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques. Ranges can be expressed herein as from one endpoint to another endpoint or between two endpoints. All ranges disclosed herein are inclusive of the endpoints, unless specified otherwise.

This present disclosure pertains generally to an anti-fibrin antibody and polypeptides comprising the same. Particularly, the anti-fibrin antibody serves as the targeting element (T) of the polypeptide, which further comprises an effector element (E), and accordingly, these polypeptides are sometimes referred to as "T-E molecules", "T-E pharmaceuticals" or "T-E drugs" in this document.

Although the terms, first, second, third, etc., may be used herein to describe various elements, components, regions, and/or sections, these elements (as well as components, regions, and/or sections) are not to be limited by these terms. Also, the use of such ordinal numbers does not imply a sequence or order unless clearly indicated by the context. Rather, these terms are simply used to distinguish one element from another. Thus, a first element, discussed below, could be termed a second element without departing from the teachings of the exemplary embodiments.

Here, the terms "link," "couple," and "conjugates" are used interchangeably to refer to any means of connecting two components either via direct linkage or via indirect linkage between two components.

The term "polypeptide" as used herein refers to a polymer having at least two amino acid residues. Typically, the polypeptide comprises amino acid residues ranging in length from 2 to about 200 residues; preferably, 2 to 50 residues. Where an amino acid sequence is provided herein, L-, D-, or beta amino acid versions of the sequence are also contemplated. Polypeptides also include amino acid polymers in which one or more amino acid residues are an artificial chemical analogue of a corresponding naturally occurring amino acid, as well as to naturally occurring amino acid polymers. In addition, the term applies to amino acids joined by a peptide linkage or by other, "modified linkages," e.g., where the peptide bond is replaced by an α-ester, a β-ester, a thioamide, phosphoramide, carbomate, hydroxylate, and the like.

In certain embodiments, conservative substitutions of the amino acids comprising any of the sequences described herein are contemplated. In various embodiments, one, two, three, four, or five different residues are substituted. The term "conservative substitution" is used to reflect amino acid substitutions that do not substantially alter the activity (e.g., biological or functional activity and/or specificity) of the molecule. Typically, conservative amino acid substitutions involve substitution one amino acid for another amino acid with similar chemical properties (e.g., charge or hydrophobicity). Certain conservative substitutions include "analog substitutions" where a standard amino acid is replaced by a non-standard (e.g., rare, synthetic, etc.) amino acid differing minimally from the parental residue. Amino acid analogs are considered to be derived synthetically from the standard amino acids without sufficient change to the structure of the parent, are isomers, or are metabolite precursors.

In certain embodiments, polypeptides comprising at least 80%, preferably at least 85% or 90%, and more preferably at least 95% or 98% sequence identity with any of the sequences described herein are also contemplated.

"Percentage (%) amino acid sequence identity" with respect to the polypeptide sequences identified herein is defined as the percentage of polypeptide residues in a candidate sequence that are identical with the amino acid residues in the specific polypeptide sequence, after aligning the sequences and introducing gaps, if necessary, to achieve the maximum percent sequence identity, and not considering any conservative substitutions as part of the sequence identity. Alignment for purposes of determining percentage sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, sequence comparison between two polypeptide sequences was carried out by computer program Blastp (protein-protein BLAST) provided online by Nation Center for Biotechnology Information (NCBI). The percentage amino acid sequence identity of a given polypeptide sequence A to a given polypeptide sequence B (which can alternatively be phrased as a given polypeptide sequence A that has a certain amino acid sequence identity to a given polypeptide sequence B) is calculated by the formula as follows:

$$\frac{X}{Y} \times 100\%$$

where X is the number of amino acid residues scored as identical matches by the sequence alignment program BLAST in that program's alignment of A and B, and where Y is the total number of amino acid residues in A or B, whichever is shorter.

The term "PEGylated amino acid" as used herein refers to a polyethylene glycol (PEG) chain with one amino group and one carboxyl group. Generally, the PEGylated amino acid has the formula of $NH_2-(CH_2CH_2O)_n-COON$. In the present disclosure, the value of n ranges from 1 to 20; preferably, ranging from 2 to 12.

As used herein, the term "terminus" with respect to a polypeptide refers to an amino acid residue at the N- or C-end of the polypeptide. With regard to a polymer, the term "terminus" refers to a constitutional unit of the polymer (e.g., the polyethylene glycol of the present disclosure) that is positioned at the end of the polymeric backbone. In the present specification and claims, the term "free terminus" is used to mean the terminal amino acid residue or constitutional unit is not chemically bound to any other molecular.

In the present specification and claims, the term "antibody" is used in the broadest sense and covers fully assembled antibodies, antibody fragments that bind with antigens, such as antigen-binding fragment (Fab/Fab'), F(ab')$_2$ fragment (having two antigen-binding Fab portions linked together by disulfide bonds), variable fragment (Fv), single chain variable fragment (scFv), bi-specific single-chain variable fragment (bi-scFv), single-domain antibodies (sdAb), nanobodies, unibodies and diabodies. "Antibody fragments" comprise a portion of an intact antibody, preferably the antigen-binding region or variable domain of the intact antibody. Typically, an "antibody" refers to a protein consisting of one or more polypeptides substantially encoded by immunoglobulin genes or fragments of immunoglobulin genes. The well-known immunoglobulin genes include the kappa, lambda, alpha, gamma, delta, epsilon, and mu constant region genes, as well as myriad immunoglobulin variable domain genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. A typical immunoglobulin (antibody) structural unit is known to comprise a tetramer. Each tetramer is composed of two identical pairs of polypeptide chains, with each pair having one "light" chain (about 25 kDa) and one "heavy" chain (about 50-70 kDa). The N-terminus of each chain defines a variable domain of about 100 to 110 or more amino acids primarily responsible for antigen recognition. The terms light-chain variable domain ($V_L$) and heavy-chain variable domain ($V_H$) refer to these light and heavy chains, respectively. According to embodiments of the present disclosure, the antibody fragment can be produced by modifying the nature antibody or by de novo synthesis using recombinant DNA methodologies. In certain embodiments of the present disclosure, the antibody and/or antibody fragment can be bispecific, and can be in various configurations. For example, bispecific antibodies may comprise two different antigen binding sites (variable domains). In various embodiments, bispecific antibodies can be produced by hybridoma technique or recombinant DNA technique. In certain embodiments, bispecific antibodies have binding specificities for at least two different epitopes.

The term "specifically binds" as used herein, refers to the ability of an antibody or an antigen-binding fragment thereof, to bind to an antigen with a dissociation constant (Kd) of no more than about $1 \times 10^{-6}$ M, $1 \times 10^{-7}$ M, $1 \times 10^{-8}$ M, $1 \times 10^{-9}$ M, $1 \times 10^{-10}$ M, $1 \times 10^{-11}$ M, $1 \times 10^{-12}$ M, and/or to bind to an antigen with an affinity that is at least two-folds greater than its affinity to a nonspecific antigen.

The term "treatment" as used herein includes preventative (e.g., prophylactic), curative or palliative treatment; and "treating" as used herein also includes preventative (e.g., prophylactic), curative or palliative treatment. In particular, the term "treating" as used herein refers to the application or administration of the present polypeptide or a pharmaceutical composition comprising the same to a subject, who has a medical condition (e.g., thrombosis) or a symptom associated with the medical condition, a disease or disorder secondary to the medical condition, or a predisposition toward the medical condition, with the purpose to partially or completely alleviate, ameliorate, relieve, delay onset of, inhibit progression of, reduce severity of, and/or reduce incidence of one or more symptoms or features of said particular disease, disorder, and/or condition. Treatment may be administered to a subject who does not exhibit signs of a disease, disorder, and/or condition, and/or to a subject who exhibits only early signs of a disease, disorder and/or condition, for the purpose of decreasing the risk of developing pathology associated with the disease, disorder and/or condition.

The term "effective amount" as used herein refers to the quantity of the present polypeptide that is sufficient to yield a desired therapeutic response. An effective amount of an agent is not required to cure a disease or condition but will provide a treatment for a disease or condition such that the onset of the disease or condition is delayed, hindered or prevented, or the disease or condition symptoms are ameliorated. The effective amount may be divided into one, two, or more doses in a suitable form to be administered at one, two or more times throughout a designated time period. The specific effective or sufficient amount will vary with such factors as particular condition being treated, the physical condition of the patient (e.g., the patient's body mass, age, or gender), the type of subject being treated, the duration of the treatment, the nature of concurrent therapy (if any), and the specific formulations employed and the structure of the compounds or its derivatives. Effective amount may be expressed, for example, as the total mass of active component (e.g., in grams, milligrams or micrograms) or a ratio of mass of active component to body mass, e.g., as milligrams per kilogram (mg/kg).

The terms "application" and "administration" are used interchangeably herein to mean the application of a polypeptide or a pharmaceutical composition of the present invention to a subject in need of a treatment thereof.

The terms "subject" and "patient" are used interchangeably herein and are intended to mean an animal including the human species that is treatable by the polypeptide, pharmaceutical composition, and/or method of the present invention. The term "subject" or "patient" intended to refer to both the male and female gender unless one gender is specifically indicated. Accordingly, the term "subject" or "patient" comprises any mammal, which may benefit from the treatment method of the present disclosure. Examples of a "subject" or "patient" include, but are not limited to, a human, rat, mouse, guinea pig, monkey, pig, goat, cow, horse, dog, cat, bird and fowl. In an exemplary embodiment, the patient is a human. The term "mammal" refers to all members of the class Mammalia, including humans, primates, domestic and farm animals, such as rabbit, pig, sheep, and cattle; as well as zoo, sports or pet animals; and rodents, such as mouse and rat. The term "non-human mammal" refers to all members of the class Mamalis except human.

The present disclosure is based, at least on the identification of an anti-fibrin antibody that binds selectively to fibrin (particularly, the fibrin clot) over fibrinogen. According to some embodiments of the present invention, the anti-fibrin antibody binds to human fibrin with an affinity 10 times better than to human fibrinogen. As such, the present anti-fibrin antibody may serve as a targeting element for the construction of a T-E molecule that localizes around the vicinity of the fibrin clot. On the other hand, the T-E molecule comprises one or more effector elements, such as those capable of breaking down pathological blood clots. In this way, the T-E pharmaceuticals can be delivered to target cells, target tissues or organs at increased proportions relative to the blood circulation, lymphoid system, and other cells, tissues or organs. When this is achieved, the therapeutic effect of the pharmaceuticals is increased, while the scope and severity of the side effects and toxicity is decreased. It is also possible that a therapeutic effector is administered at a lower dosage in the form of a T-E molecule, than in a form without a targeting component. Therefore, the therapeutic effector can be administered at lower dosages without losing potency, while lowering side effects and toxicity.

In view of the foregoing, one aspect of the present disclosure is directed to an anti-fibrin antibody, which can distinguish fibrin clots from fibrinogen. Although other anti-fibrin antibodies have been developed, none can discriminate between fibrin clots and fibrinogen at a sufficient extent to yield clinical applications. Therefore, the production of a monoclonal antibody that can distinguish a fibrin clot from fibrinogen is be a major breakthrough for the development of T-E pharmaceuticals targeting pathological blood clots.

According to embodiments of the present disclosure, the anti-fibrin antibody comprises a light-chain variable domain (VL) and a heavy-chain variable domain (VH) respectively having the amino acid sequence of SEQ ID NOs: 1 and 2, SEQ ID NOs: 17 and 18, SEQ ID NOs: 19 and 20, or SEQ ID NOs: 21 and 22. According to some embodiments, the VL domain and VH domain respectively comprise three complementarity-determining regions (CDRs). Specifically, the CDR-L1, and CDR-L2, and CDR-L3 of the present anti-fibrin antibody have the amino acid sequences corresponding to residues 30 to 32, residues 49 to 54, and residues 91 to 96 of SEQ ID NO: 1, respectively. Also, the DR-H1, and CDR-H2, and CDR-H3 of the present anti-fibrin antibody have the amino acid sequences corresponding to residues 30 to 33, residues 50 to 59, and residues 98 to 106 of SEQ ID NO: 2, respectively.

According to various embodiments of the present disclosure, the anti-fibrin antibody can be an intact antibody or an antibody fragment that comprises antigen-binding region or variable domain (e.g., the above-mentioned CDRs). For example, the antibody may me provided as a single-chain variable fragment (scFv) or a single-domain antibody (sdAb). However, the present disclosure is not limited thereto.

In some optional embodiments, the anti-fibrin antibody comprises a light-chain variable domain having the amino acid sequence of SEQ ID NO: 1 and a heavy-chain variable domain having the amino acid sequence of SEQ ID NO: 2.

According to some optional embodiments of the present disclosure, a linker sequence is arranged between the VL and VH or VH and VL sequences so as to increase the half-life and/or binding affinity of the present scFv. For example, the linker sequence mat be a hydrophilic sequence. In some optional embodiments, the anti-fibrin antibody may be an scFv having the amino acid sequences of SEQ ID NO. 3 or 5.

In another aspect, the present disclosure is directed to a polypeptide. In particular, the polypeptide is a T-E pharmaceutical that comprises a targeting element (e.g., the anti-fibrin antibody according to the above-mentioned aspect/embodiments of the present disclosure) and an effector element for treating thrombosis (e.g., a tissue plasminogen activator). Therefore, methods for treating thrombosis using such polypeptides are also encompassed in the scope of the present disclosure.

According to various embodiments of the present disclosure, the polypeptide comprises the anti-fibrin antibody and a serine protease moiety of human tissue plasminogen activator (hu-tPA) that is linked to the N- or C-terminus of the anti-fibrin antibody, directly or indirectly via a linker.

An illustrative example of the serine protease moiety of hu-tPA is reteplase. Other polypeptides equivalent to reteplase are also included in the scope of the present disclosure.

In some embodiments, the anti-fibrin antibody and the serine protease moiety of hu-tPA are linked directly, while in other cases, the two are linked indirectly with an intervening sequence disposed therebetween. According to certain embodiments of the present disclosure, a hydrophilic linker sequence is arranged between the anti-fibrin antibody and the serine protease moiety of hu-tPA to facilitate the binding of the polypeptide with the fibrin meshwork in the clot. For example, when the serine protease moiety of hu-tPA is linked to the N-terminus of the anti-fibrin antibody, the polypeptide has the amino acid sequence of SEQ ID NO. 11 or 12. Alternatively, when the serine protease moiety of hu-tPA is linked to the C-terminus of the anti-fibrin antibody, the polypeptide has the amino acid sequence of SEQ ID NO. 14.

According to some embodiments, the present polypeptide binds to human fibrin better than the hu-tPA does. Alternatively, or additionally, the present polypeptide has a longer serum half-life in an animal than reteplase does.

EXPERIMENTAL EXAMPLES

Example 1: Preparation of Human Fibrin-Coated Plate for Phage-Displayed Screening To prepare fibrin-coated plates, fibrinogen from human (Sigma) diluted with PBS was added to a Maxi soap plate (Nunc) at 10 μg/100 μL per well, and the plate was sealed and allowed to stand at 4° C., overnight.

Each fibrin plate was prepared as follows. 100 μL of Tris-buffered saline (TBS) containing a final concentration of 1.0 U/mL thrombin (Sigma), 2 mM CaCl, and 7 mM L-cysteine (Merck) was added to the wells of the fibrinogen plate, which was then washed with TBS buffer and blocked with 5% skim milk in PBST (phosphate-buffered saline with 0.1% tween-20).

Example 2: Construction and Selection of Phage-Displayed scFv Specific for Human Fibrin The phage clones carrying the scFv specific for human fibrin were obtained through a contractual arrangement with Dr. An-Suei Yang's laboratory at the Genomics Research Center, Academia Sinica, Taipei, Taiwan. The framework sequence of the scFv library was derived from G6 anti-VEGF Fab (Protein Bank Code 2FJG) and cloned into restriction sites Sfil and NotI of phagemid vector pCAN-TAB5E (GE Healthcare) carrying an ampicillin resistance, a lacZ promotor, a pelB leader sequence for secretion of scFv fragments into culture supernatants, and an E-tag applicable for detection shown in the $V_H$ and $V_L$ domains of the scFv template were diversified separately based on the oligonucleotide-directed mutagenesis procedure; the 3 CDRs in each of the variable domains were diversified simultaneously. The scFv library of over $10^9$ clones was used for selections on human fibrin.

Maxisorp 96-well plates (Nunc) coated with digested human fibrin (1 μg/100 μL PBS per well) were used for panning anti-fibrin antibodies. Briefly, the wells were coated with human fibrin by shaking the coating solution in the wells for 2 hours at room temperature. The fibrin-coated wells were then treated with blocking buffer (5% skim milk in PBST with 0.1% tween-20) for 1 hour at room temperature. Recombinant phages in the blocking buffer diluted to $8 \times 10^{11}$ CFU/ml were added to the fibrin-coated wells for 1 hour with gentle shaking. The wells were then washed vigorously 10 times with PBST, followed by 6 times with PBS to remove nonspecific binding phages. The bound phages were eluted using 0.1 M HCl/glycine buffer at pH 2.2, and the elution solution was neutralized immediately by 2 M Tris-base buffer at pH 9.0. E. coli strain ER2738 (OD600=~0.6) was used for phage infection at 37° C. for 30 minutes; non-infected E. coli was eliminated by treating with ampicillin for 30 minutes. Thereafter, the helper phage M13KO7 with kanamycin resistance was added for another 1-hour incubation. The selected phages rescued by the helper phage in the E. coli culture were amplified with vigorously shaking overnight at 37° C. in the presence of kanamycin. The amplified phages were precipitated in PEG/NaCl and then resuspended in PBS for the next selection-amplification cycles. A total of three consecutive panning rounds was performed on human fibrin by repeating this selection-amplification procedure.

The thrombin-treated fibrin plates (1 μg/100 μL per well) were prepared as described in the preceding Examples. The fibrin plates were used for panning anti-fibrin antibodies. In brief, the fibrin-coated wells were treated with blocking buffer (5% skim milk in PBST with 0.1% tween-20) for 1 hour at the room temperature. Recombinant phages in the blocking buffer diluted to $8 \times 10^{11}$ CFU/ml were added to the fibrin-coated wells for 1 hour with gentle shaking. The wells were then washed vigorously 10 times with PBST, followed by 6 times with PBS to remove nonspecific binding phages. The bound phages were eluted using 0.1 M HCl/glycine buffer at pH 2.2, and the eluted fraction was neutralized immediately by 2 M Tris-base buffer at pH 9.0. E. coli strain ER2738 (OD600=~0.6) was used for phage infection at 37° C. for 30 minutes; non-infected E. coli was eliminated by treating with ampicillin for 30 minutes. Thereafter, the helper phage M13KO7 with kanamycin resistance was added for another 1-hour incubation. The selected phages rescued by the helper phage in the E. coli culture were amplified with vigorously shaking overnight at 37° C. in the presence of kanamycin. The amplified phages were precipitated in PEG/NaCl, and then resuspended in PBS for the next selection-amplification cycle. A total of three consecutive panning rounds were performed on human fibrin by repeating this selection-amplification procedure.

Phage-infected ER2738 colonies that were enumerated by serial dilution were counted, and phage titers were calculated, yielding the output titer/ml (CFU/ml) per panning round. A 1000-fold increase in phage output title from 1.6E+04 CFU/well to 2.2E+07 CFU/well was obtained after three rounds of panning. The phage output/input titer ratios from each round are shown in FIG. 1A. For each panning round, the phage output/input titer ratios are given on the y-axis. There was a clear enrichment of the positive clones over the three rounds of panning. The third panning round resulted in a 100-fold of increase of the ratios of phage output/input titer compared with the first round, as the binding clones became the dominant population in the library.

In a typical selection procedure, after three rounds of antigen-panning on human fibrin-coated wells in ELISA plates, approximately 80% of the bound phage particles bound to fibrin specifically in ELISA with coated fibrin.

Example 3: Single Colony ELISA Analysis of Phage-Displayed scFvs Specific for Human Fibrin E. coli strain ER2738 infected with single-clonal phages each harboring a selected scFv gene in its phagemid was grown in the mid-log phase in 2YT broth (16 g/L tryptone, 10 g/l yeast extract, 5 g/l NaCl, pH 7.0) with 100 μg/ml ampicillin in deep well at 37° C. with shaking. After broth reaching an $OD_{600}$ of 1.0, IPTG was added to a final concentration of 1 μg/ml. The plates were incubated at 37°

C. overnight with rigorously shaking. Thereafter, the plates were centrifuged at 4,000 g for 15 minutes at 4° C.

Figure 1B:
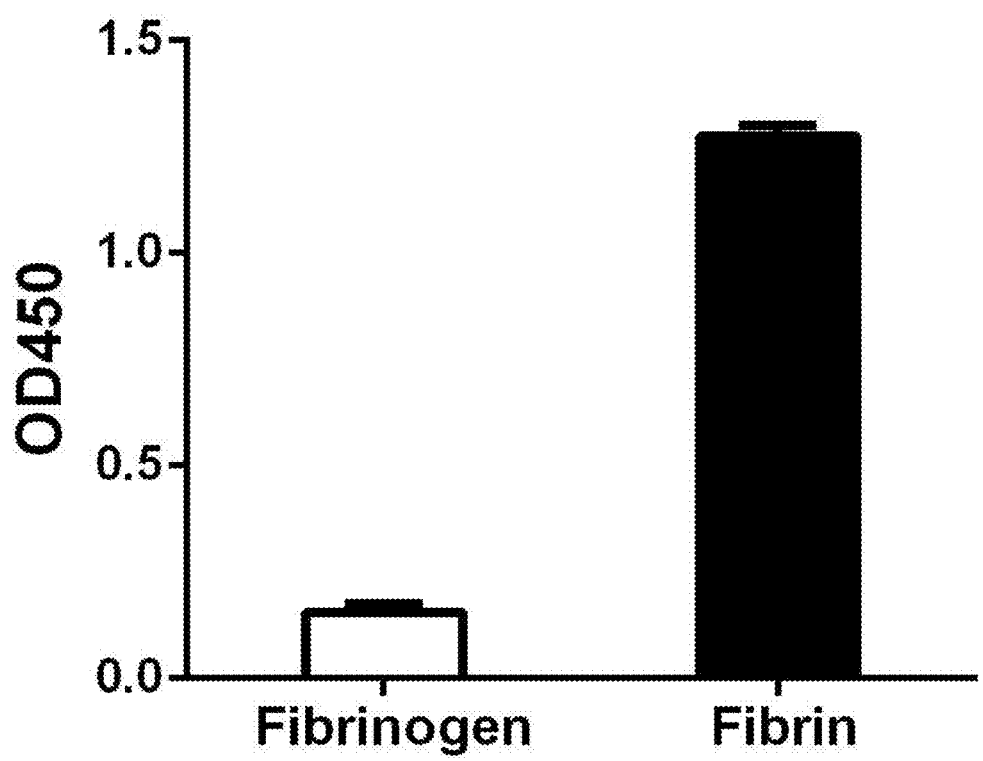
FIG. 1B shows the result of single colony ELISA analysis of phage-displayed D10 scFvs specific for human fibrin.

For soluble scFv binding test, ELISA was carried out. In brief, 96-well Maxisorp 96-well plate (Nunc) was coated with fibrin (0.5 µg/100 µL PBS per well) or a negative control antigen, human fibrinogen, for 18 hours with shaking at 4° C. After treated with 300 µL of blocking buffer for one hour, 100 µL of secreted scFv in the supernatant was mixed with 100 µL of blocking buffer and then added to the coated plate for another one hour. Goat anti-E-tag antibody (conjugated with HRP, 1:4000, Cat. No. AB19400, Abcam) was added to the plate for one hour. TMB substrate (50 µL per well) was added to each well and the absorbance at 450 nm was measured after reactions were stopped by adding 1 N HCl (50 µL per well). The $OD_{450}$ for each well was measured to determine the binding affinity of each scFv clone to fibrin or fibrinogen. For each scFv clone, the $OD_{450}$ value with respect to fibrin was divided by with the $OD_{450}$ value with respect to fibrinogen to obtain an $OD_{450}$ ratio representing the selective binding of said scFv to fibrin over fibrinogen. In the single colony ELISA analysis, a total of 192 phage clones after the $3^{rd}$ panning round was subjected to the present analysis. Among them, 12 scFv clones that bound to fibrin with an $OD_{450}$ ratio greater than 10 were further characterized by sequencing their scFv-coding gene. Six different DNA sequences were identified. FIG. 1B shows the ELISA result of an scFv clone D10. The amino acid sequence of an scFv clone D10, which binds to human fibrin with an $OD_{450}$ of 1.3, is shown in SEQ ID NO: 4.

An addition round of selection was conducted following the protocol set forth above. This time, a 1000-fold increase in phage output title from 9.3E+04 CFU/well to 4.5E+07 CFU/well was obtained after three rounds of panning. The third panning round resulted in a 130-fold on the ratios of phage output/input titer over the first round, as the binding clones became the dominant population in the library. A total of 192 phage clones after the $3^{rd}$ panning round was subjected to the present analysis. Among them, 18 scFv clones that bound to fibrin with an $OD_{450}$ ratio greater than 10 were further characterized by sequencing their scFv-coding gene. Four different DNA sequences were identified, and the $OD_{450}$ data and sequences of these four clones were summarized in Table 1 below.

TABLE 1

|  | 3C2 | 8F2 | 3D5 | 7A3 |
|---|---|---|---|---|
| $OD_{450}$_Fibrin | 0.7588 | 0.5273 | 0.8294 | 0.4285 |
| $OD_{450}$_Fibrinogen | 0.0117 | 0.0366 | 0.0022 | 0.0209 |
| $OD_{450}$ ratio | 64.8547 | 14.4071 | 377 | 20.50239 |
| $V_L$ | SEQ ID NO: 17 | SEQ ID NO: 19 | SEQ ID NO: 1 | SEQ ID NO: 21 |
| $V_H$ | SEQ ID NO: 18 | SEQ ID NO: 20 | SEQ ID NO: 2 | SEQ ID NO: 22 |

The scFv with the highest $OD_{450}$ ratio, 3D5 scFv was subjected to subsequent analysis, and the amino acid sequence of the phage-displayed 3D5 scFv is shown in SEQ ID NO: 5.

Example 4: Preparation of Recombinant Anti-Fibrin 102-10 Antibody and Anti-Fibrin 3D5 Antibody The $V_L$ and $V_H$ fragments of the 3D5 antibody specific for human fibrin were placed in pG1K expression vector for expression. The amino acid sequences of the light chain and heavy chain of the full-length antibody are shown in SEQ ID NO: 8 and 9, respectively.

The $V_H$ and $V_L$ fragments of the 102-10 antibody (Japanese Patent Application Publication No. 2012-72) were placed in pG1K expression vector for expression. The amino acid sequences of the light chain and heavy chain of the full-length antibody are shown in SEQ ID NO: 6 and 7, respectively.

To prepare recombinant antibodies using a mammalian expression system, the overexpression system based on Expi293F™ cell line was used. The system employed ExpiFectamine™ 293 transfection kit (Life Technologies, Carlsbad, USA) consisting of the Expi293F™ cell line, the cationic lipid-based ExpiFectamine™ 293 Reagent and ExpiFectamine™ 293 transfection Enhancers 1 and 2, and the medium, which was part of the expression system (Gibco, New York, USA).

Expi293F cells were seeded at a density of $2.0 \times 10^6$ viable cells/ml in Expi293F expression medium and maintained for 18 to 24 hours prior to transfection to ensure that the cells were actively dividing at the time of transfection. At the time of transfection, $7.5 \times 10^8$ cells in 255 ml medium in a 2-liter Erlenmeyer shaker flask were transfected by ExpiFectamine™ 293 transfection reagent. The transfected cells were incubated at 37° C. for 16 to 18 hours post-transfection in an orbital shaker (125 rpm) and the cells were added ExpiFectamine™ 293 transfection enhancer 1 and enhancer 2 to the shaker flask, and then incubated for 5 to 6 days. Culture supernatants were harvested and the antibodies in the media were purified using Protein A affinity chromatography.

Example 5: ELISA Analysis of the Binding of 102-10 and 3D5 Antibodies to Human Fibrinogen, Fibrin and the Crosslinked Fibrin Treated by Human Factor XIIIa To examine the binding abilities of 102-10 and 3D5 antibodies to human fibrinogen, fibrin and crosslinked fibrin, ELISA analysis was performed.

To prepare fibrin-coated plates, human fibrinogen (Sigma) diluted with PBS was added to a 96-well polystyrene microplate at 100 µL/well, and the plate was sealed and allowed to stand at 4° C., overnight.

Each fibrin plate was prepared as follows. 100 µL of TBS containing a final concentration of 1.0 U/mL thrombin (Sigma), 2 mM CaCl, and 7 mM L-cysteine (Merck) was added to the wells of the fibrinogen plate, which was then washed with TBS and blocked with the buffer (5% non-fat dry milk/PBS). After the blocking, 100 µL of antibodies were added to each well, and the plate was incubated at room temperature for 1 hour. The plate was then washed three times, the HRP-conjugated protein L diluted to 1/5000 was added to the wells and incubated for 1 hour at room temperature. The wells were washed three times and added with 100 µL of TMB substrate buffer. 5 minutes later, the color development was stopped with 1 M HCl. The optical density (OD) was measured at 450 nm using a microplate reader.

Figure 2:
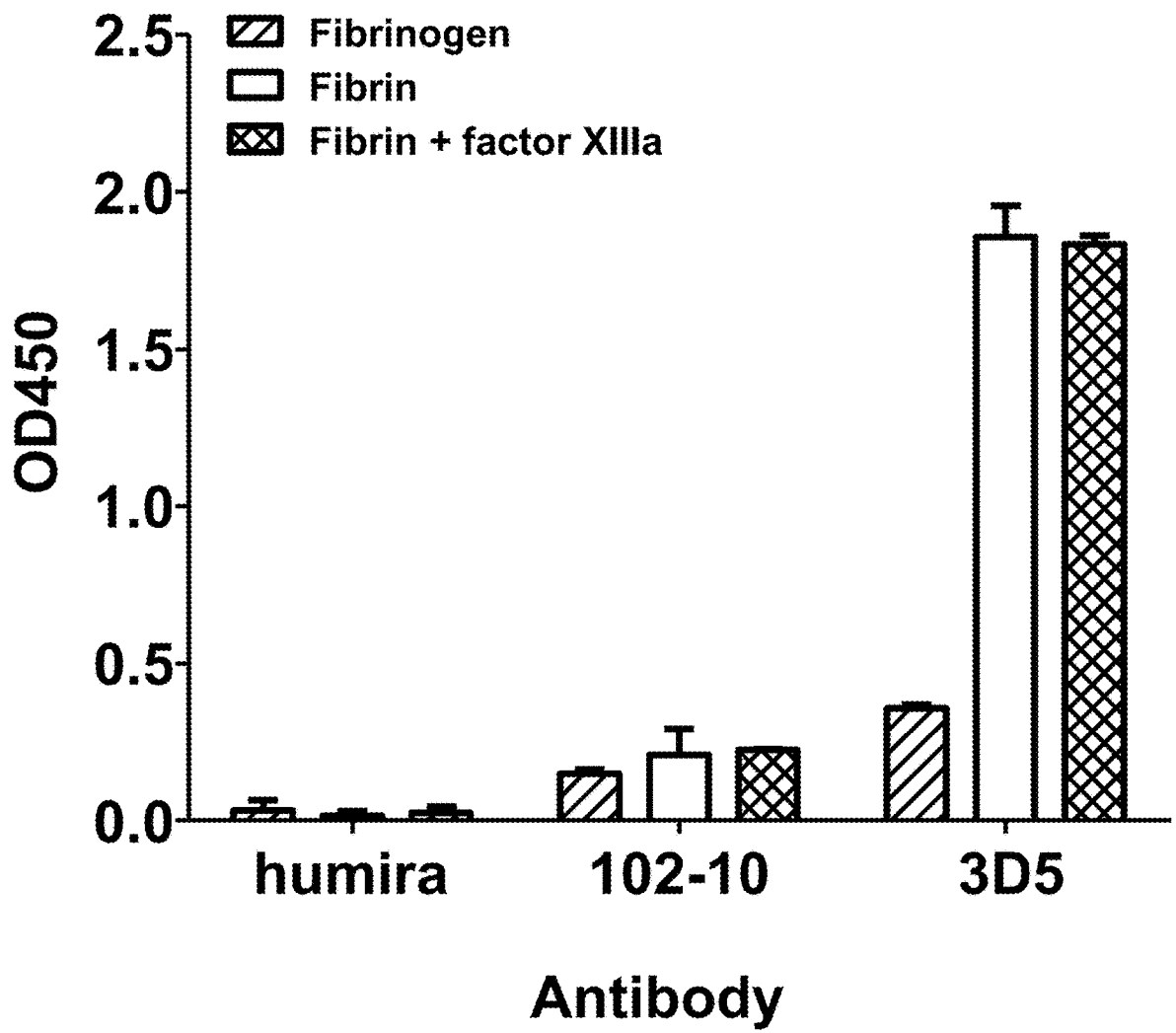
FIG. 2 shows the result of the ELISA analysis of the purified 102-10 and 3D5 antibodies specific for human fibrin.

The ELISA results were summarized in FIG. 2, which indicate that the 3D5 antibody can bind to human fibrin or the crosslinked fibrin stronger than 102-10 antibody does.

Example 6: Preparation of Polypeptide Containing Reteplase and 102-10 scFv Specific for Human Fibrin in the $V_L$-218 Linker-$V_H$ Configuration The (reteplase)-102-10 scFv polypeptide was configured by fusing reteplase to the N-terminus of the 102-10 scFv through a flexible linker (SEQ ID NO: 15, hereinafter, flexible linker). The 102-10 scFv had an orientation of $V_L$-linker-$V_H$, wherein the two domains were connected by a hydrophilic 218 linker, GSTSGSGKPGSGEGSTKG (SEQ ID NO: 16). The sequence of the recombinant polypeptide is shown in SEQ ID NO: 10.

The configuration of the present (reteplase)-(102-10 scFv α fibrin) polypeptide is illustrated below.

Reteplase scFv α fibrin

Example 7: Expression and Purification of Recombinant (Reteplase)-(scFv α Fibrin) by Expi293F Overexpression System The scFv-encoding sequence was placed in pcDNA3 expression cassette. The expression of the constructed gene in Expi293F cells and the purification of the expressed polypeptide were carried out using the protocol described in preceding Examples.

Figure 3:
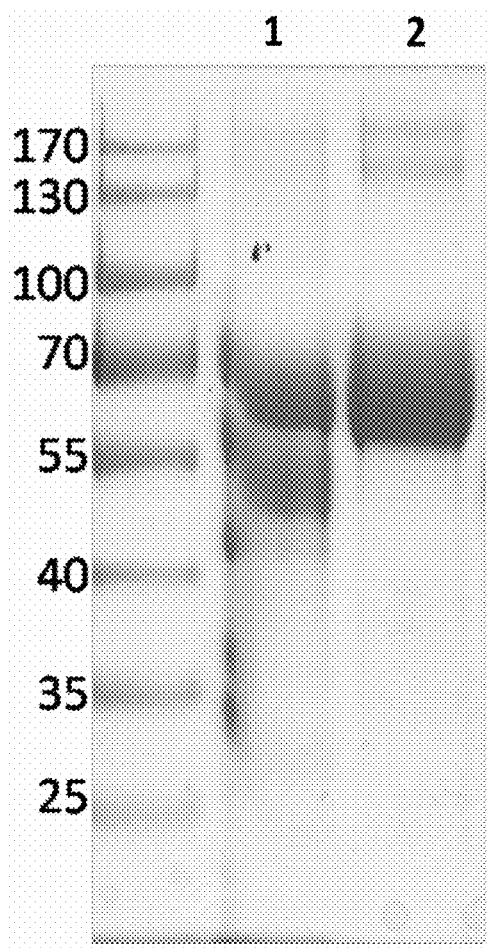
FIG. 3 shows the result of SDS-PAGE analysis of purified recombinant reteplase-(3D5 VL-flexible linker-VH scFv α fibrin) and reteplase-(102-10 scFv α fibrin).

Characterization of the new construct was carried out using SDS-PAGE. The 10% non-reducing SDA-PAGE results in FIG. 3 shows that the recombinant (reteplase)-(102-10 scFv α fibrin) protein (lane 2) has a major band at about 71 kDa, consistent with the expected size.

Example 8: Preparation of Polypeptide Containing Reteplase and 3D5 scFv Specific for Human Fibrin in the $V_L$-Flexible Linker Linker-$V_H$ Configuration The recombinant reteplase-(3D5 $V_L$-flexible linker-$V_H$ scFv α fibrin) protein was configured by fusing reteplase to the N-terminus of the 3D5 scFv specific for human fibrin through a flexible linker.

The scFv had an orientation of $V_L$-linker-$V_H$, and the two domains were connected by a flexible linker. The sequence of the recombinant polypeptide is shown in SEQ ID NO: 11. Characterization of the new construct was carried out using SDS-PAGE. The 10% non-reducing SDA-PAGE results in FIG. 3 shows that the sample in lane 1 has the expected product at about 71 kDa; however, an unexpected degraded product is also found at about 55 kDa.

Example 9: Preparation of Polypeptide Containing Reteplase and 3D5 scFv Specific for Human Fibrin in the $V_L$-218 Linker-$V_H$ Configuration The recombinant reteplase-(3D5 $V_L$-218-$V_H$ scFv α fibrin) protein (hereinafter, reteplase-(3D5 scFv)) was configured by fusing reteplase to the N-terminus of the 3D5 scFv specific for human fibrin through a flexible linker.

Figure 4:
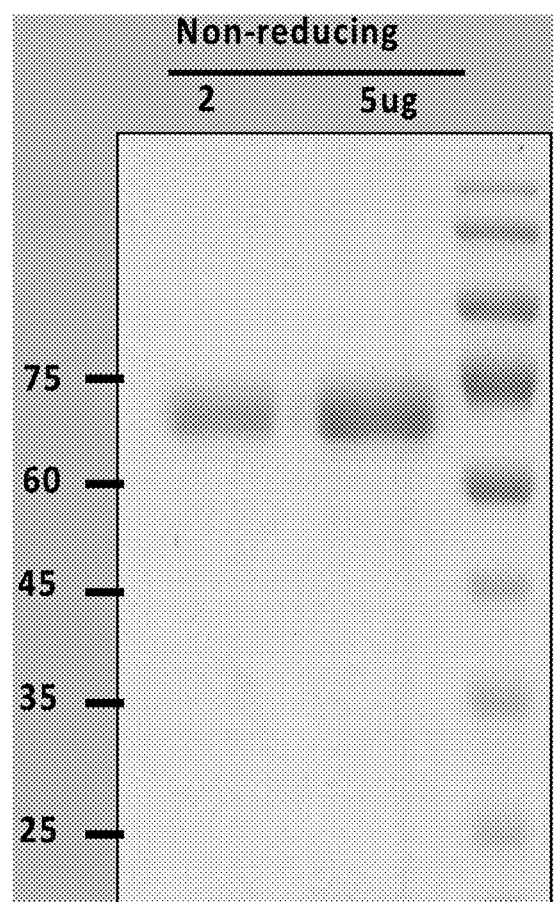
FIG. 4 shows the result of SDS-PAGE analysis of the purified recombinant reteplase-(3D5 VL-218-VH scFv α fibrin).

The scFv had an orientation of $V_L$-linker-$V_H$. and the two domains were connected by a hydrophilic 218 linker. The sequence of the recombinant polypeptide is shown in SEQ ID NO: 12. Characterization of the new construct was carried out using SDS-PAGE. The 10% non-reducing SDA-PAGE results in FIG. 4 shows that the recombinant chain of the new construct (lane 1 and lane 2) has a size of about 71 kDa, consistent with the expected size. Since the reteplase-(3D5 scFv) prepared in this Example is more stable than the reteplase-(3D5 $V_L$-flexible linker-$V_H$ scFv α fibrin) polypeptide of the previous Example, in the following Examples, the present reteplase-(3D5 scFv) was subjected to further analyses.

Example 10: Preparation of Recombinant Reteplase-IgG4.Fc Protein Using Expi293F Overexpression System The reteplase-CH2-CH3 (human γ4) recombinant chain was configured by fusing reteplase to the N-terminus of CH2 domain of IgG4.Fc through a flexible hinge region. The sequence of the recombinant chain in the IgG4.Fc polypeptide is shown in SEQ ID NO: 13.

The expression of the constructed gene in Expi293F cells of the expressed polypeptide was performed as described in preceding Examples.

Example 11: Stability Analysis of Reteplase-(3D5 scFv) Using SDS-PAGE

To evaluate the stability of reteplase-(3D5 scFv) after storage, the reteplase-(3D5 scFv) was stored at 4° C. for 3, 6 and 30 days, and then SDS-PAGE and ELISA analysis were performed.

Figure 5A:
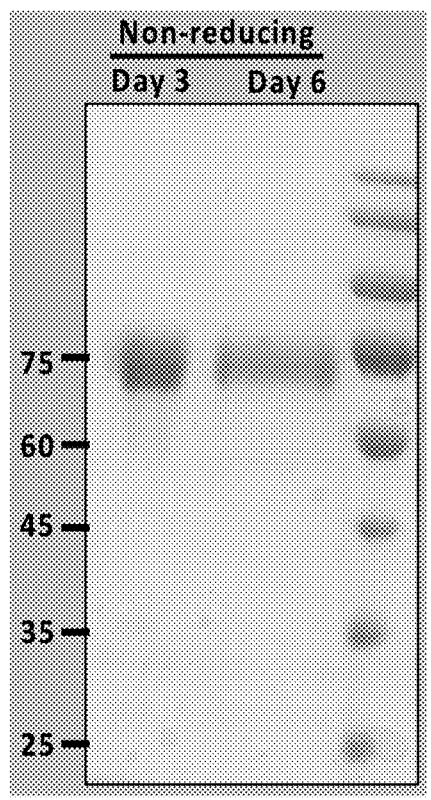
FIG. 5A shows the result of SDS-PAGE analysis of the purified recombinant reteplase-(3D5 scFv) stored for three or six days.
Figure 5B:
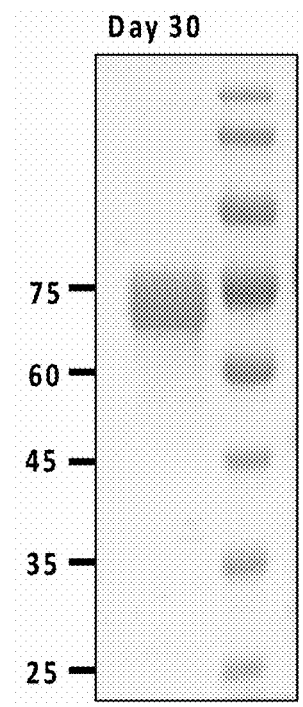
FIG. 5B shows the result of SDS-PAGE analysis of the purified recombinant reteplase-(3D5 scFv) stored for one month.

The 10% non-reducing SDS-PAGE results were summarized in FIGS. 5A and 5B, indicating that the recombinant reteplase-(3D5 scFv) polypeptide is stable for at least one month.

To examine the binding ability of the stored reteplase-(3D5 scFv) polypeptides to human fibrin, ELISA assay was performed.

96-well polystyrene microplates were coated with human fibrinogen (Sigma) (20 μg/mL) in PBS buffer (100 μL/well). After overnight incubation at 4° C., the coated wells were washed with PBS buffer. To induce the cross-linking of human fibrin, coated wells was incubated at 37° C. for 1 hour with human α-thrombin (Sigma) at a final concentration of 1 U/mL in TBS buffer with 2 mM $CaCl_2$ and 7 mM L-cystine (Merck). After blocking the wells with a blocking buffer (5% non-fat dry milk/PBS), 100 μL of reteplase-(3D5-scFv) at a final concentration of 0.1, 1 and 10 μg/mL were added to each well and incubate at room temperature for 1 hour. Thereafter, the plates were washed three times, and HRP-conjugated protein L diluted to 1/5000 was added to the wells and incubated for 1 hour at room temperature. The wells were washed three times and added with 100 μL of 3,3',5,5'-Tetramethylbenzidine (TMB) substrate buffer. 5 minutes later, the color development was stopped with 1 M HCl. The optical density (OD) was measured at 450 nm using a microplate reader (Molecular Devices) and the data were processed using Graph Pad Prism software.

As for preparing the crosslinked fibrin plate treated with factor XIIIa, the procedures for coating were similar to the procedures described with respect to the fibrin-coated plate. Briefly, fibrinogen from human (Sigma) diluted with PBS was added to a 96-well polystyrene microplate at 100 µL/well, and the plate was then sealed and allowed to stand at 4° C., overnight.

Each fibrin plate was prepared as follows. 100 µL of TBS containing a final concentration of 1.0 U/mL thrombin (Sigma), 0.55 µg factor XIIIa (Zedira, Darmstadt, Germany) per well, 2 mM $CaCl_2$ and 7 mM L-cysteine (Merck) was added to the wells of the fibrinogen plate, which was then washed with TBS and blocked with the buffer (5% non-fat dry milk/PBS).

Figure 5C:
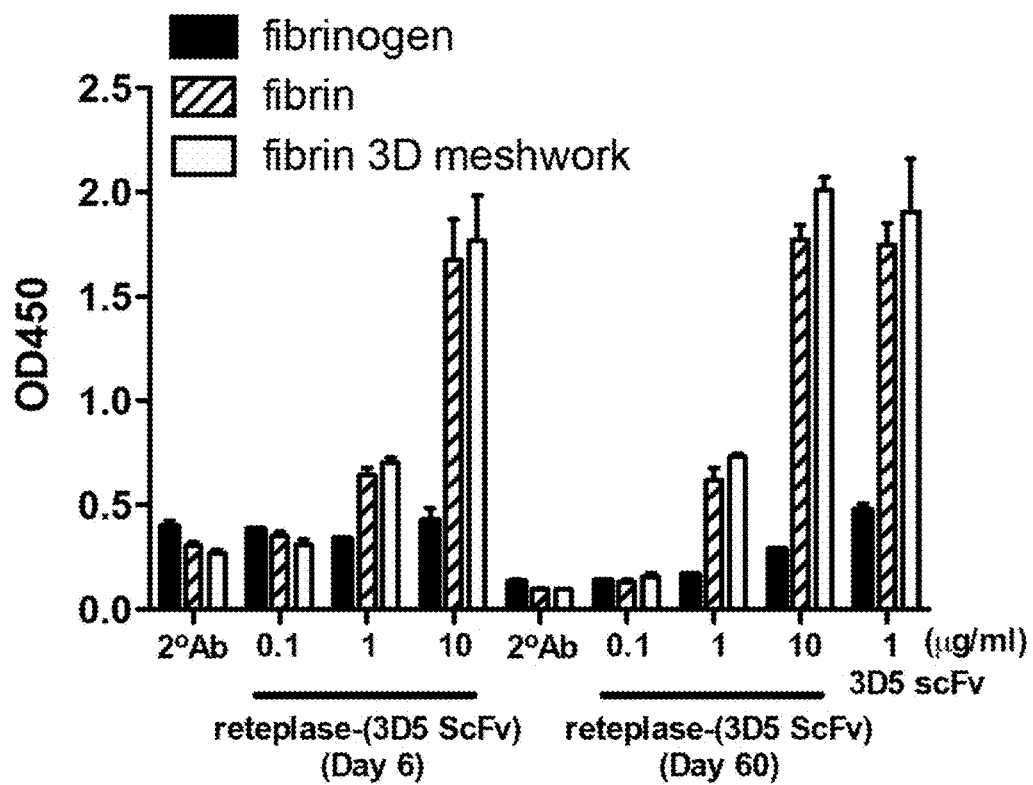
FIG. 5C shows the result of ELISA analysis of the purified recombinant reteplase-(3D5 scFv) stored for three or six days.

Recombinant reteplase-(3D5 scFv) polypeptides were detected using HRP-conjugated protein L. The ELISA results were summarized in FIG. 5C, which indicate that even after the designated storage period, the reteplase-(3D5 scFv) can still bind to human fibrin and the crosslinked fibrin specifically.

Example 12: ELISA Analysis of the Human Fibrin and Crosslinked Fibrin Binding of (Reteplase)-(3D5 scFv) Polypeptides To investigate the dose-dependency of the human fibrin binding ability of recombinant reteplase-(3D5 scFv) polypeptides, ELISA assay was undertaken.

The procedures for ELISA analysis were similar to the procedures described in the previous Examples. Briefly, fibrinogen from mouse (Sigma) diluted with PBS was added to a 96-well polystyrene microplate at 100 µL/well, and then the plate was sealed and allowed to stand at 4° C., overnight.

Each fibrin plate was prepared as follows. 100 µL of TBS containing a final concentration of 1.0 U/mL thrombin (Sigma), 2 mM $CaCl_2$ and 7 mM L-cysteine (Merck) was added to the wells of the fibrinogen plate, which was then washed with TBS and blocked with the buffer (5% non-fat dry milk/PBS). Thereafter, 100 µL of reteplase-(3D5-scFv) at various final concentrations (600 nM, 200 nM, 66 nM, 22 nM, 7.4 nM, 2.5 nM, and 0.8 nM) were added to each well and incubate at room temperature for 1 hour. The plate was than washed for three times, and HRP-conjugated protein L diluted to 1/5000 was added to the wells and incubated for 1 hour at room temperature. The wells were washed three times and added with 100 µL of TMB substrate buffer. 5 minutes later, the color development was stopped with 1 M HCl. The optical density (OD) was measured at 450 nm using a microplate reader.

Figure 6:
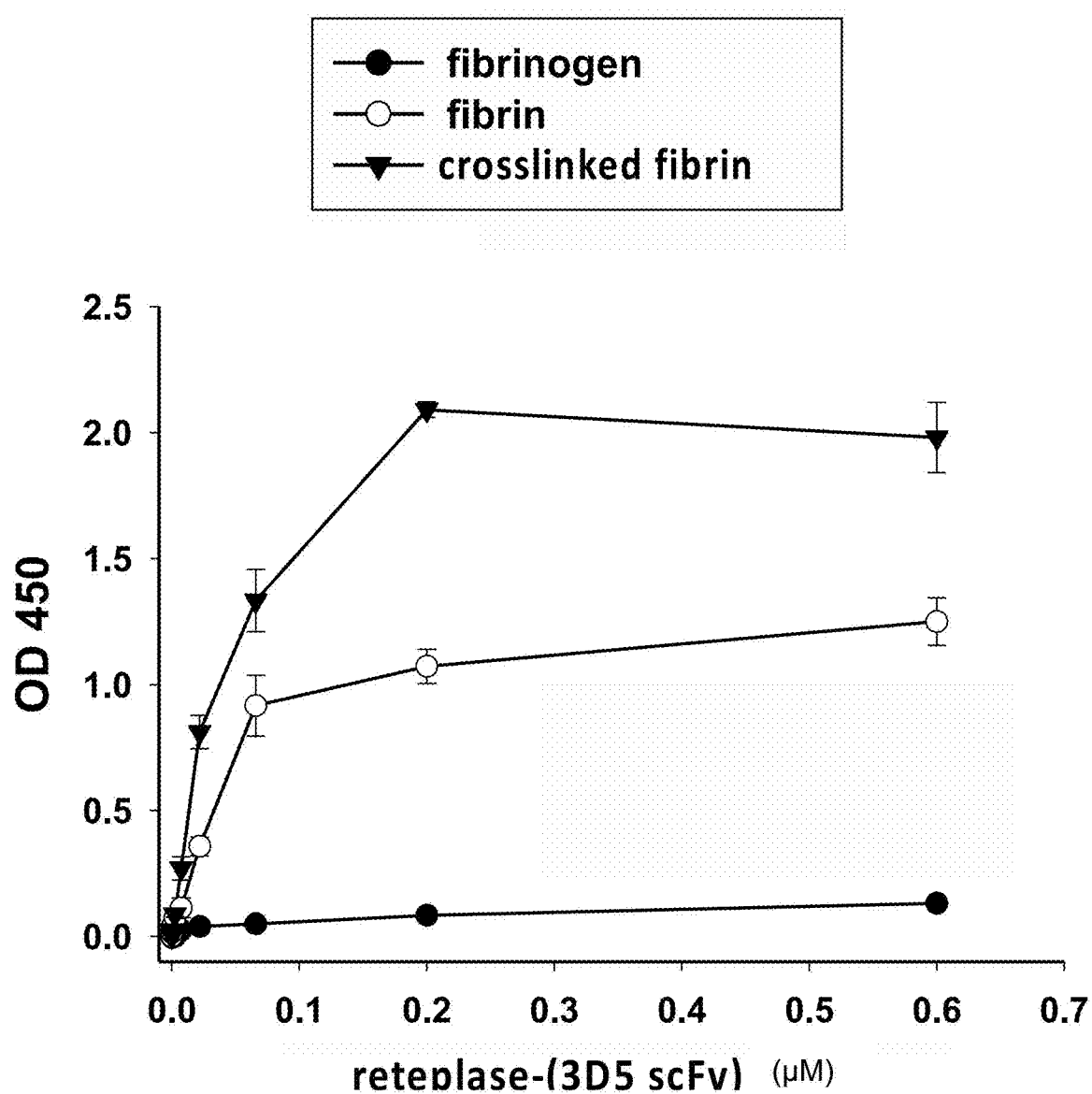
FIG. 6 shows the result of ELISA analysis of reteplase-(3D5 scFv) polypeptides to human fibrin and to the cross-linked fibrin treated by human factor XIIIa.

Recombinant reteplase-(3D5 scFv) polypeptides were detected using HRP-conjugated protein L. The ELISA results summarized in FIG. 6 indicate that the reteplase-(3D5 scFv) polypeptide binds specifically to human fibrin and the crosslinked fibrin; however, it has a stronger binding ability to the crosslinked fibrin than to fibrin.

Example 13: ELISA Analysis of Mouse Fibrin Binding of Recombinant Reteplase-(3D5 scFv) Polypeptide To check the binding ability of recombinant reteplase-(3D5 scFv) polypeptides to mouse fibrin by ELISA, mouse fibrin-coated ELISA plates were prepared.

To prepare the mouse fibrin plate, the procedures for coating were similar to the procedures described with respect to human fibrin-coated plate. Briefly, fibrinogen from mouse (Sigma) diluted with PBS was added to a 96-well polystyrene microplate at 100 µL/well, and the plate was sealed and allowed to stand at 4° C., overnight.

Each fibrin plate was prepared as follows. 100 µL of TBS containing a final concentration of 1.0 U/mL thrombin (Sigma), 2 mM $CaCl_2$ and 7 mM L-cysteine (Merck) was added to the wells of the fibrinogen plate, which was then washed with TBS and blocked with the buffer (5% non-fat dry milk/PBS). Thereafter, 100 µL of reteplase-(3D5-scFv) at a final concentration of 200 nM were added to each well and incubate at room temperature for 1 hour. The plate was then washed three times, and HRP-conjugated protein L diluted to 1/5000 was added to the wells and incubated for 1 hour at room temperature. The wells were washed three times and added with 100 µL of TMB substrate buffer. 5 minutes later, the color development was stopped with 1 M HCl. The optical density (OD) was measured at 450 nm using a microplate reader.

Figure 7:
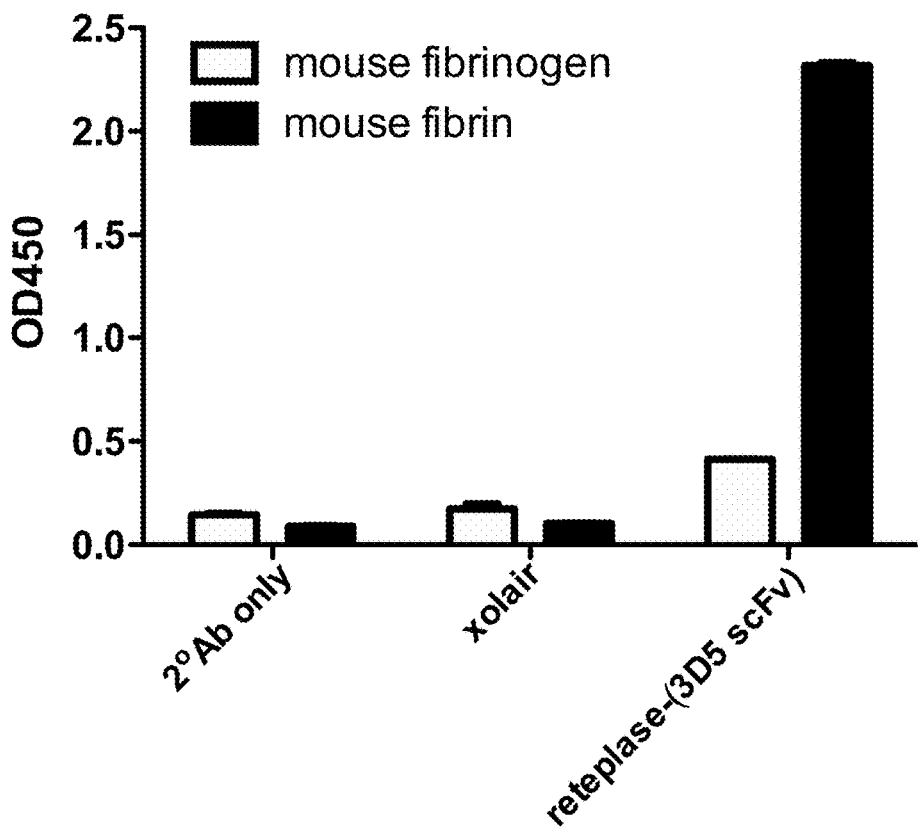
FIG. 7 shows the result of ELISA analysis of the binding of recombinant reteplase-(3D5 scFv) polypeptides to mouse fibrin.

Xolair is an antibody against IgE and was used herein as a negative control. Recombinant reteplase-(3D5 scFv) polypeptides and reteplase were detected using HRP-conjugated protein L. The ELISA results summarized in FIG. 7 indicate that the reteplase-(3D5 scFv) binds specifically to mouse fibrin, but not to mouse fibrinogen.

Example 14: ELISA Analysis of Human Fibrin Binding of Recombinant Reteplase-(3D5 scFv) Polypeptide in the Presence of Free Fibrinogen To assess the binding ability of recombinant reteplase-(3D5 scFv) polypeptides to human fibrin in the presence of 200 mg/dl or 400 mg/dl human fibrinogen, ELISA analysis was performed and the procedure was similar to those described in preceding Examples.

Briefly, human fibrinogen diluted with PBS was added to a 96-well polystyrene microplate at 100 µL/well, and the plate was then sealed and allowed to stand at 4° C., overnight.

Each fibrin plate was prepared as follows. 100 µL of TBS containing a final concentration of 1.0 U/mL thrombin (Sigma), 2 mM $CaCl_2$ and 7 mM L-cysteine (Merck) was added to the wells of the fibrinogen plate, which was then washed with TBS and blocked with the buffer (5% non-fat dry milk/PBS). Thereafter, 100 µL of reteplase-(3D5-scFv) at a final concentration of 200 nM, which was mixed with human fibrinogen at a final concentration of 200 mg/dl or 400 mg/dl, were added to each well and incubated at room temperature for 1 hour. The plate was then washed three times, and HRP-conjugated protein L diluted to 1/5000 was added to the wells and incubated for 1 hour at room temperature. The wells were washed three times and added with 100 µL of TMB substrate buffer. 5 minutes later, the color development was stopped with 1 M HCl. The optical density (OD) was measured at 450 nm using a microplate reader.

Figure 8:
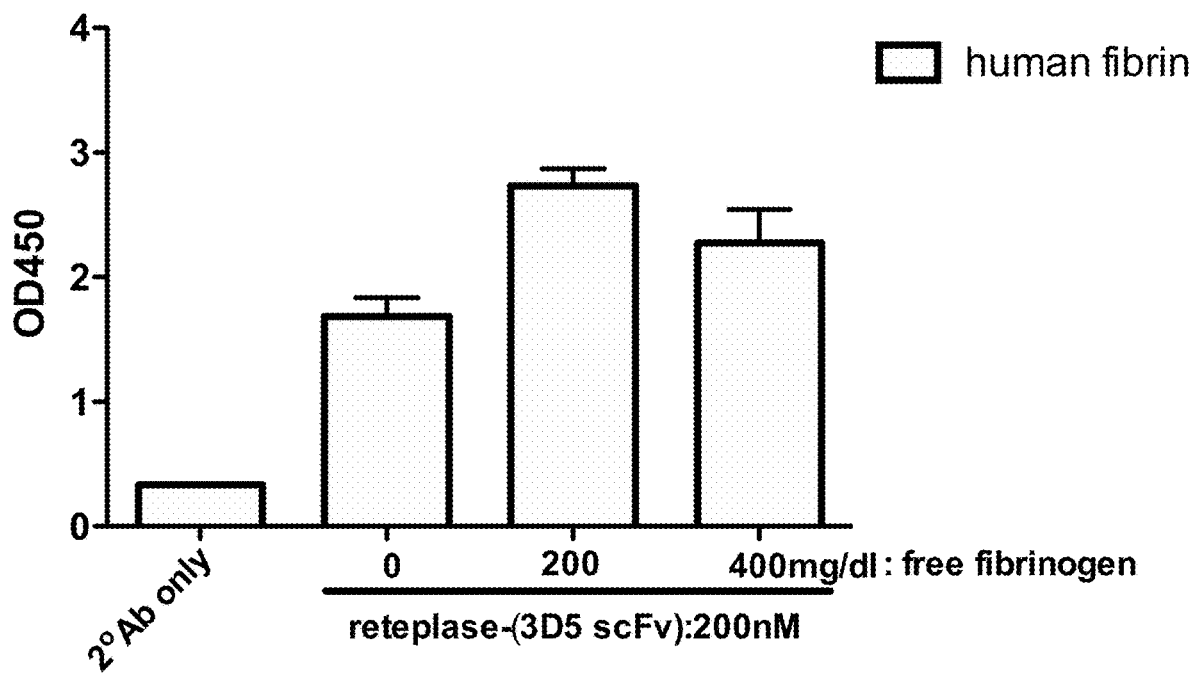
FIG. 8 shows the result of ELISA analysis of the binding of recombinant reteplase-(3D5 scFv) polypeptides to human fibrin in the presence of free fibrinogen.

Recombinant reteplase-(3D5 scFv) polypeptides and reteplase were detected using HRP-conjugated protein L. The ELISA results summarized in FIG. 8 indicate that the reteplase-(3D5 scFv) polypeptides binds specifically to human fibrin in the presence of free fibrinogen at a final concentration of 200 mg/dl or 400 mg/dl.

Example 15: Thrombolytic Activity of Recombinant Reteplase-(3D5 scFv) Polypeptide in PBS or Human Serum To examine thrombolytic activities, a whole blood thrombolytic plate assay was performed. Briefly, human blood was collected from healthy volunteer via venipuncture into tri-sodium citrate at a final concentration of 3.2% w/v. Clot formation was induced with thrombin. A clotting mixture was freshly prepared from thrombin (final conc. of 6.25×

$10^{-3}$U) and calcium chloride at a final concentration of 67 mM in HEPES buffer (25 mM HEPES, 137 mM NaCl). 5 µL of the clotting mixture was deposited onto the bottom edge of the well of a 96-well microplate (Costar), followed by the addition of 25 µL of blood. The plate was then sealed and incubated at 37° C. for 1 hour, and blood clots were formed around the edge of the wells.

Reteplase-IgG4.Fc and reteplase-(3D5-scFv) were diluted into 70 µL of PBS. The 70-µL samples were added simultaneously into the wells containing the human clots at room temperature for 3 minutes with a multichannel pipette. After removing samples, 70 µL of human serum or PBS were added into the wells and the degradation of the human clots was determined using a microplate reader (Molecular Devices) by measuring the absorbance at 510 nm as the blood from the dissolved clot gradually covers the center of the well. The data were processed using Graph Pad Prism software.

Figure 9:
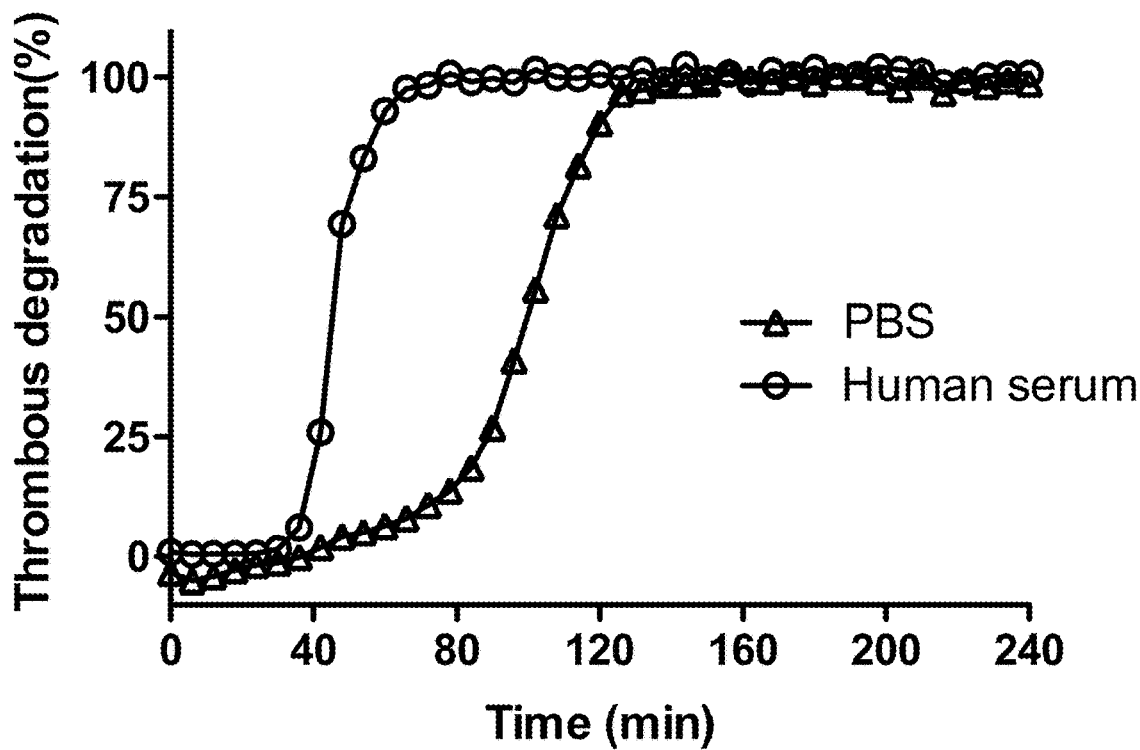
FIG. 9 shows the thrombolytic activity of recombinant reteplase-(3D5 scFv) polypeptides in the PBS or human serum.

The results of thrombolytic assay summarized in FIG. 9 indicate that the reteplase-(3D5 scFv) has a better thrombolytic activity in the human serum than in PBS.

Example 16: Thrombolytic Activity of Recombinant Reteplase-(3D5 scFv) Polypeptide at a Final Concentration of 1 mM Reteplase-IgG4.Fc and reteplase-(3D5-scFv) were diluted into 70 µL of PBS at a final concentration of 1 nM. The 70-µL samples were added simultaneously into the wells containing the human clots at room temperature for 3 minutes with a multichannel pipette. After removing samples, 70 µL of human serum was added into the wells and the degradation of the human clots was determined using a microplate reader (Molecular Devices) by measuring the absorbance at 510 nm as the blood from the dissolved clot gradually covers the center of the well. The data were processed using Graph Pad Prism software.

Figure 10:
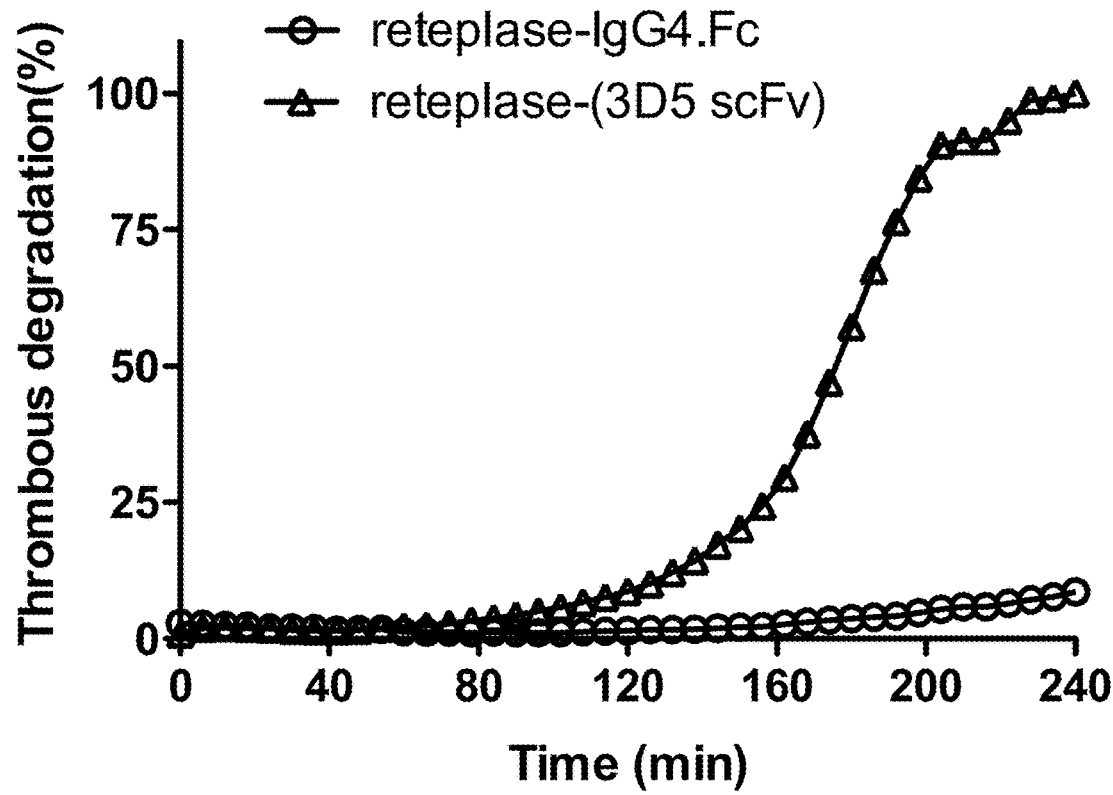
FIG. 10 shows the thrombolytic activity of recombinant reteplase-(3D5 scFv) polypeptides at a final concentration of 1 mM.

The results of thrombolytic assay summarized in FIG. 10 indicate that the reteplase-(3D5 scFv) has a better thrombolytic activity at a final concentration of 1 mM than reteplase-IgG4.Fc does.

Example 17: Targeting Effect of Recombinant Reteplase-(3D5 scFv) Polypeptide

Reteplase-IgG4.Fc and reteplase-(3D5-scFv) were diluted into 70 µL of PBS at a final concentration of 30 nM. The 70-µL samples were added simultaneously into the wells containing the human clots at room temperature for 3 minutes with a multichannel pipette. After removing samples and washing the clot three times with 250 µL PBS, 70 µL of human serum was added into the wells and the degradation of the human clots was determined using a microplate reader (Molecular Devices) by measuring the absorbance at 510 nm as the blood from the dissolved clot gradually covers the center of the well. The data were processed using Graph Pad Prism software.

Figure 11:
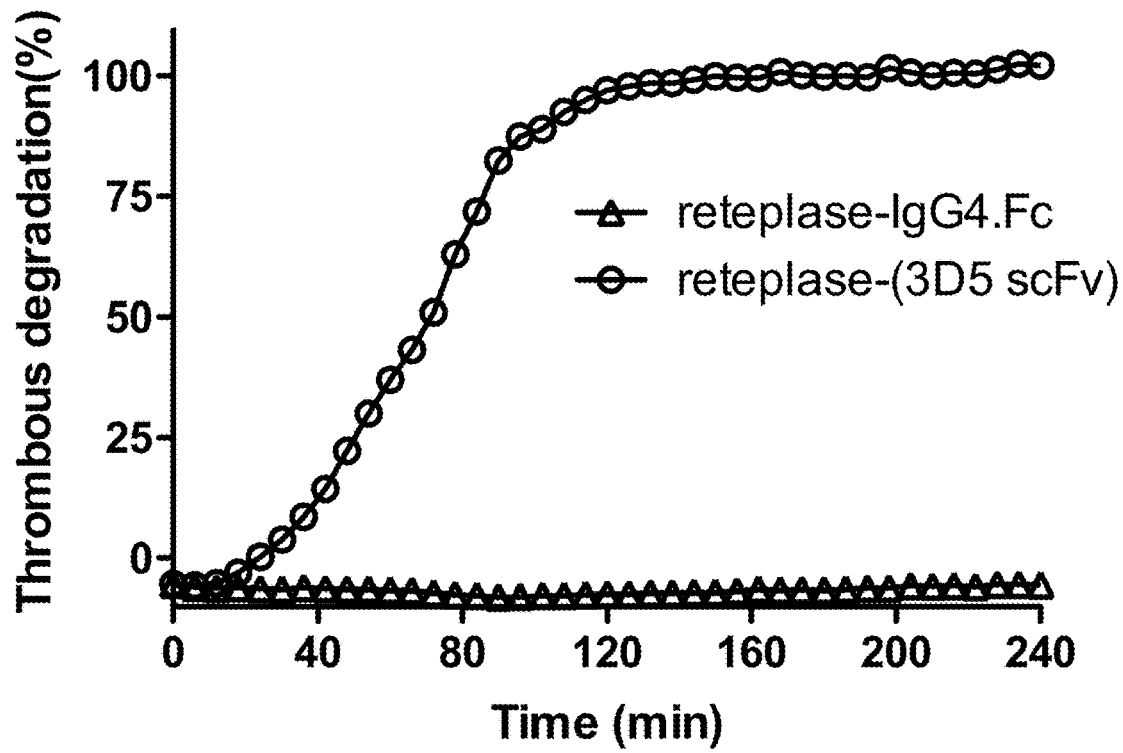
FIG. 11 shows targeting effect of recombinant reteplase-(3D5 scFv) polypeptides.

The results of the assay summarized in FIG. 11 indicate that the reteplase-(3D5 scFv) targets to human clots and still exhibits the desired thrombolytic activity even after the washing treatment. In contrast, the control protein, reteplase-IgG4.Fc, exhibits no targeting function and nearly no thrombolytic activity after the washing treatment.

Example 18: Dose-Dependent Thrombolytic Activity of Recombinant Reteplase-(3D5 scFv) Polypeptide Reteplase-(3D5-scFv) polypeptide was diluted into 70 µL of PBS at final concentrations of 5 nM, 10 nM, 20 nM and 30 nM, and reteplase-IgG4.Fc was diluted into 70 µL of PBS at final concentration of 30 nM. The 70-µL sample was added simultaneously into the wells containing the human clots at room temperature for 3 minutes with a multichannel pipette. After removing samples and washing the clot three times with 250 µL PBS, 70 µL of human serum was added into the wells and the degradation of the human clots was determined using a microplate reader (Molecular Devices) by measuring the absorbance at 510 nm as the blood from the dissolved clot gradually covers the center of the well. The data were processed using Graph Pad Prism software.

Figure 12:
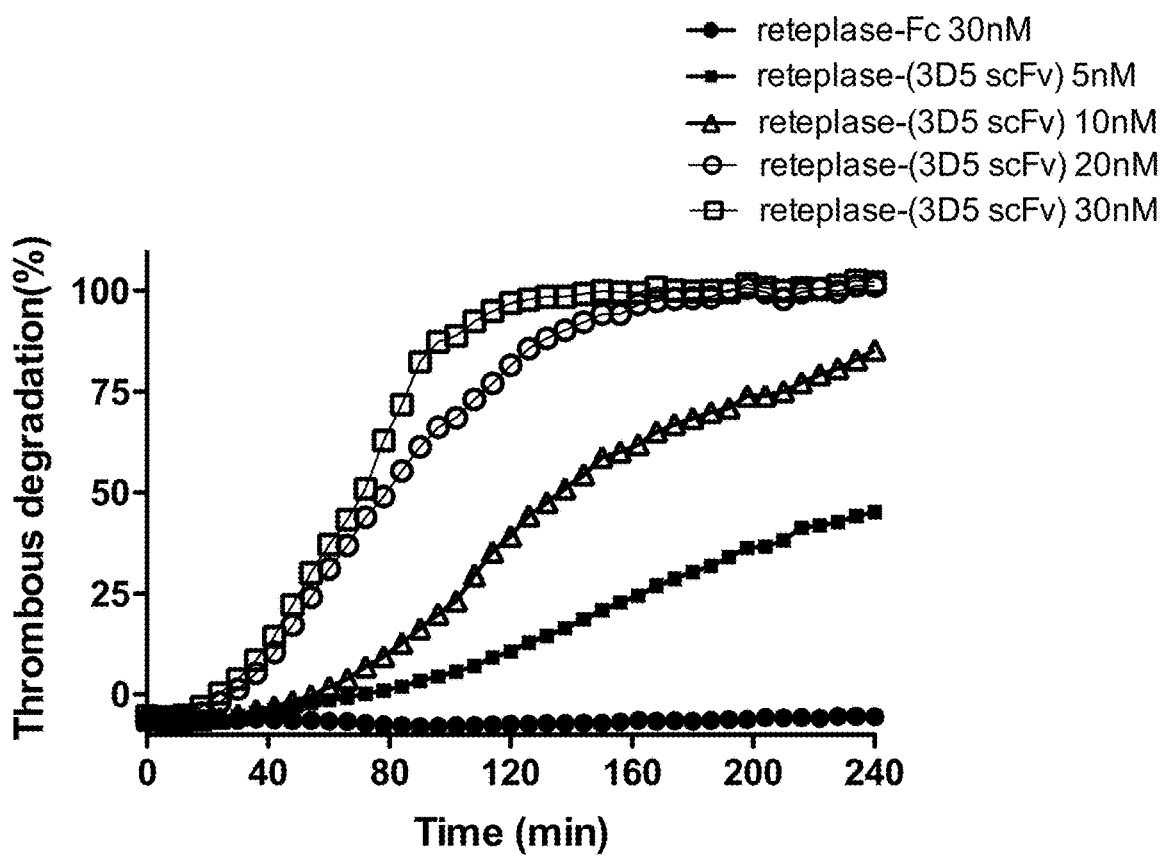
FIG. 12 shows the dose-dependent thrombolytic activity of recombinant reteplase-(3D5 scFv).

The results of the assay summarized in FIG. 12 indicate that the present reteplase-(3D5 scFv) targets to human clots and exhibits the desired thrombolytic activity even at a concentration as low as 5 nM. On the other hand, reteplase-IgG4.Fc had no thrombolytic activity even at the concentration of 30 nM.

Example 19: Dose-Dependent Thrombolytic Activities of Recombinant Reteplase-(3D5 scFv) Polypeptide and Reteplase to Human Clot To compare thrombolytic activities of recombinant reteplase-(3D5 scFv) polypeptides and reteplase (MIRel®, purchased from Reliance Life Science) to human clot, whole blood thrombolytic assay was performed with a procedure similar to the one described in preceding Examples.

Reteplase and reteplase-(3D5-scFv) polypeptide were diluted into 70 µL of PBS at final concentrations of 5 nM, 10 nM, 20 nM and 30 nM. The 70-µL sample was added simultaneously into the wells containing the human clots at room temperature for 3 minutes with a multichannel pipette. After removing samples and washing the clot three times with 250 µL PBS, 70 µL of human serum was added into the wells and the degradation of the human clots was determined using a microplate reader (Molecular Devices) by measuring the absorbance at 510 nm as the blood from the dissolved clot gradually covers the center of the well. The data were processed using Graph Pad Prism software.

Figure 13A:
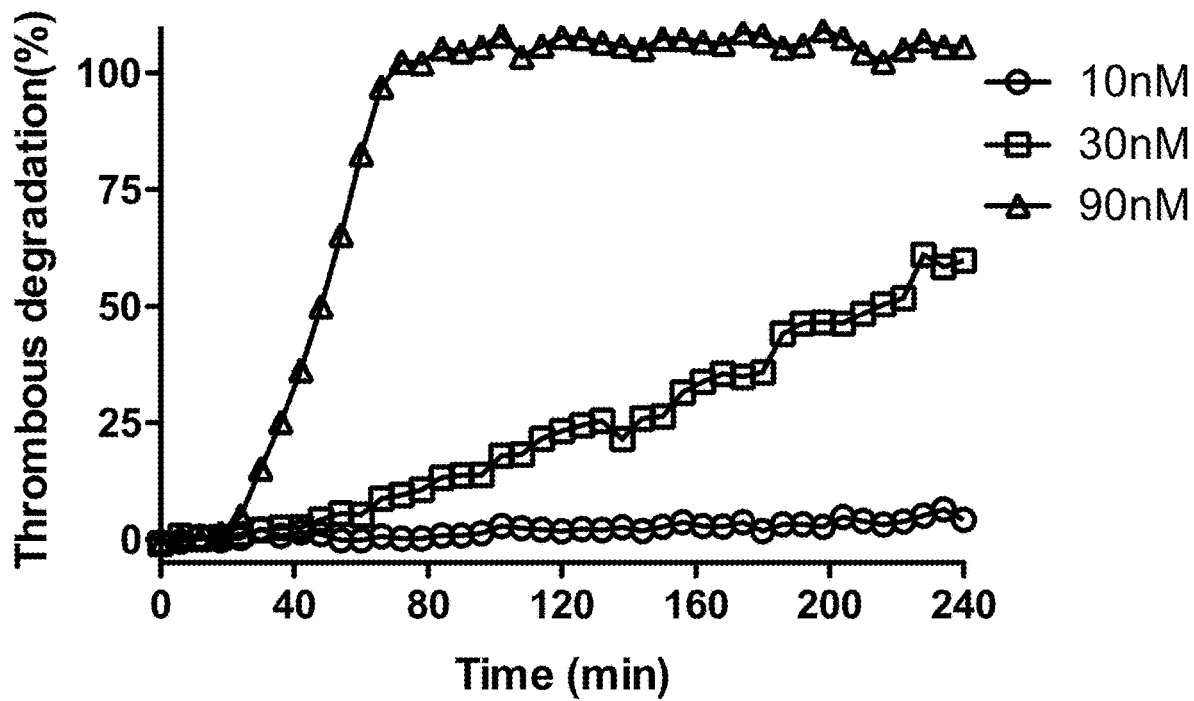
FIGS. 13A to 13C demonstrate the thrombolytic activity reteplase-(3D5 scFv) to human clots.
Figure 13B:
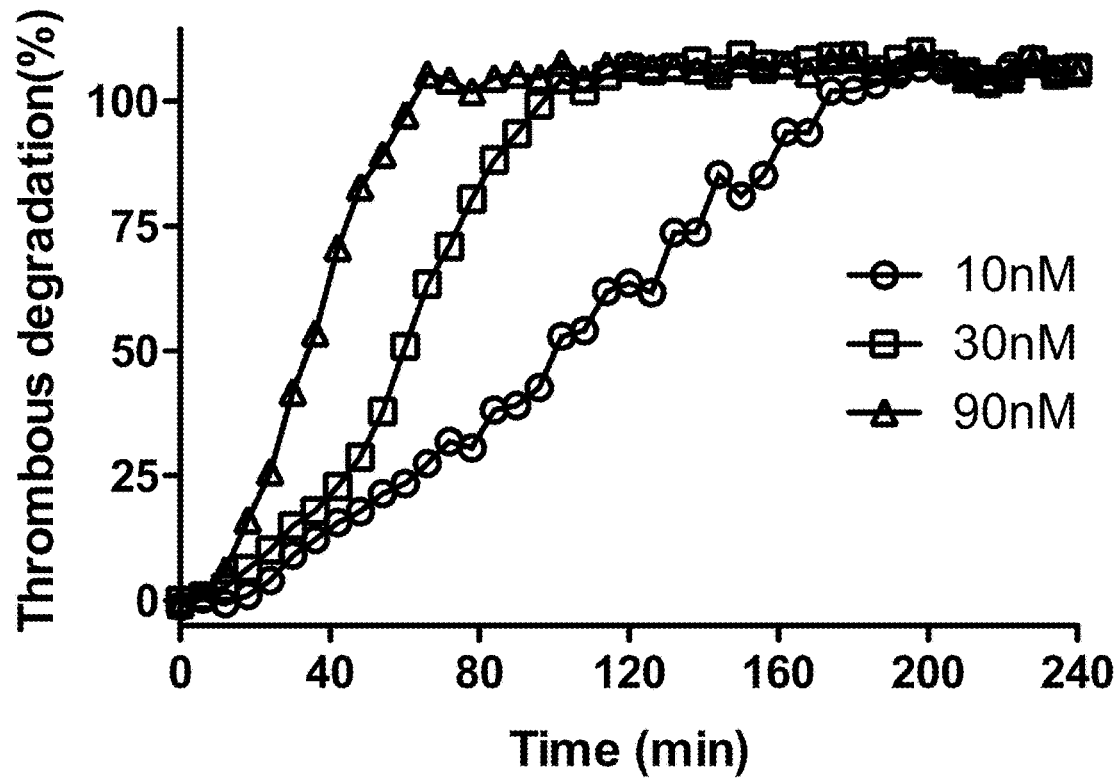

The results of the assays in FIGS. 13A and 13B indicate that the reteplase (FIG. 13A) and reteplase-(3D5 scFv) polypeptide (FIG. 13B) exhibit the thrombolytic activity at the concentration of 10 nM, 30 nM and 90 nM in human plasma.

Figure 13C:
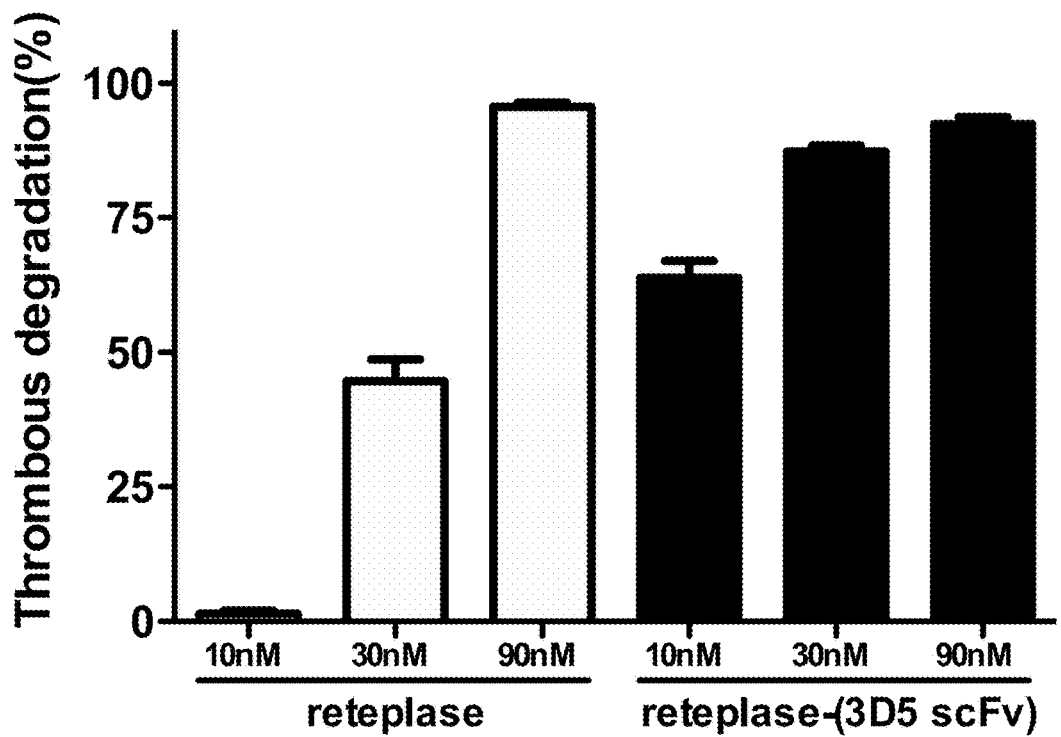

The results of the assay summarized in FIG. 13C indicate that the recombinant reteplase-(3D5 scFv) polypeptide exhibits a better thrombolytic activity than reteplase does at the concentration of 10 nM, 30 nM and 90 nM in human plasma.

Example 20: Thrombolytic Activity of Recombinant Reteplase-(3D5 scFv) Polypeptide to Monkey Clot Monkey blood was purchased from National Defense University (Taipei, Taiwan). Monkey clot formation was induced with human thrombin and the procedure was similar to those described in preceding Examples. Briefly, a clotting mixture was freshly prepared from thrombin (final conc. of $6.25 \times 10^{-3}$U) and calcium chloride at final concentrations of 67 mM in HEPES buffer (25 mM HEPES, 137 mM NaCl). 5 µL of the clotting mixture was deposited onto the bottom edge of the well of a 96-well microplate (Costar), followed by the addition of 25 µL of blood. The plate was then sealed and incubated at 37° C. for 1 hour, and monkey blood clots were formed around the edge of the wells.

Reteplase-(3D5-scFv) were diluted into 70 µL of PBS. The 70-µL samples were added simultaneously into the wells containing the monkey clots at room temperature for 3 minutes with a multichannel pipette. After removing samples, 70 µL of human plasma or PBS were added into the wells and the degradation of the monkey clots was determined using a microplate reader (Molecular Devices) by measuring the absorbance at 510 nm as the blood from the dissolved clot gradually covers the center of the well. The data were processed using Graph Pad Prism software.

Figure 14A:
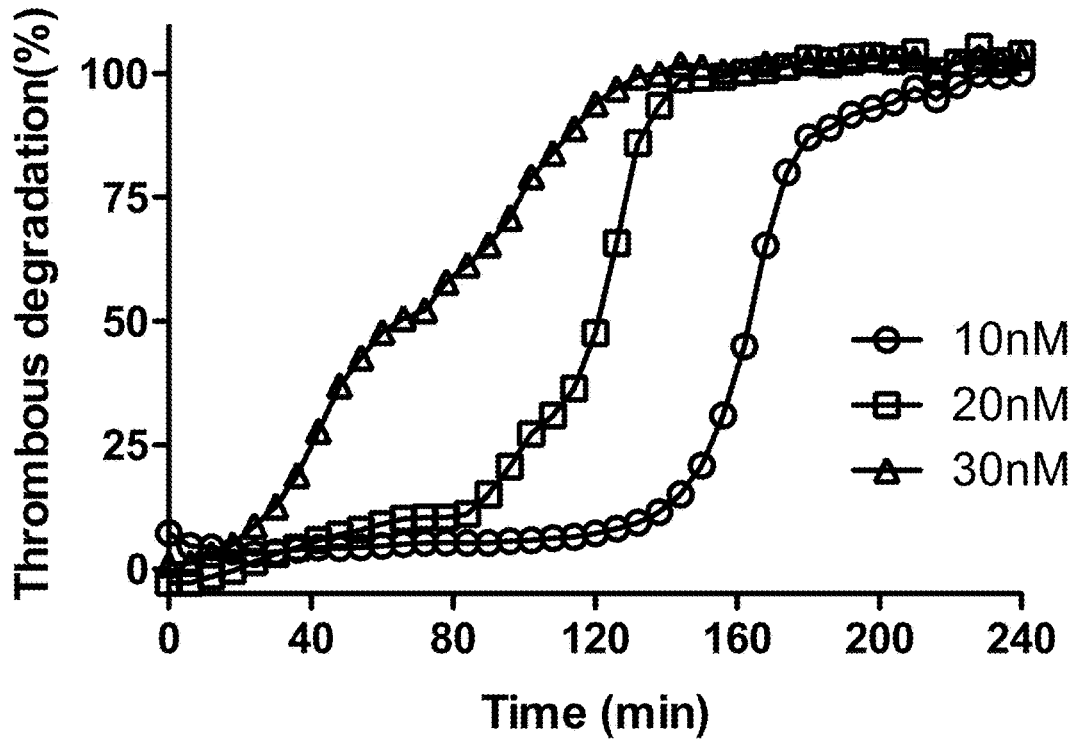
FIGS. 14A and 14B demonstrate the thrombolytic activity of reteplase-(3D5 scFv) to monkey clots.

The results of thrombolytic assay summarized in FIG. 14A indicate that the present reteplase-(3D5 scFv) polypeptide, at the concentrations of 10 nM, 20 nM and 30 nM, can dissolve monkey clots in PBS.

Figure 14B:
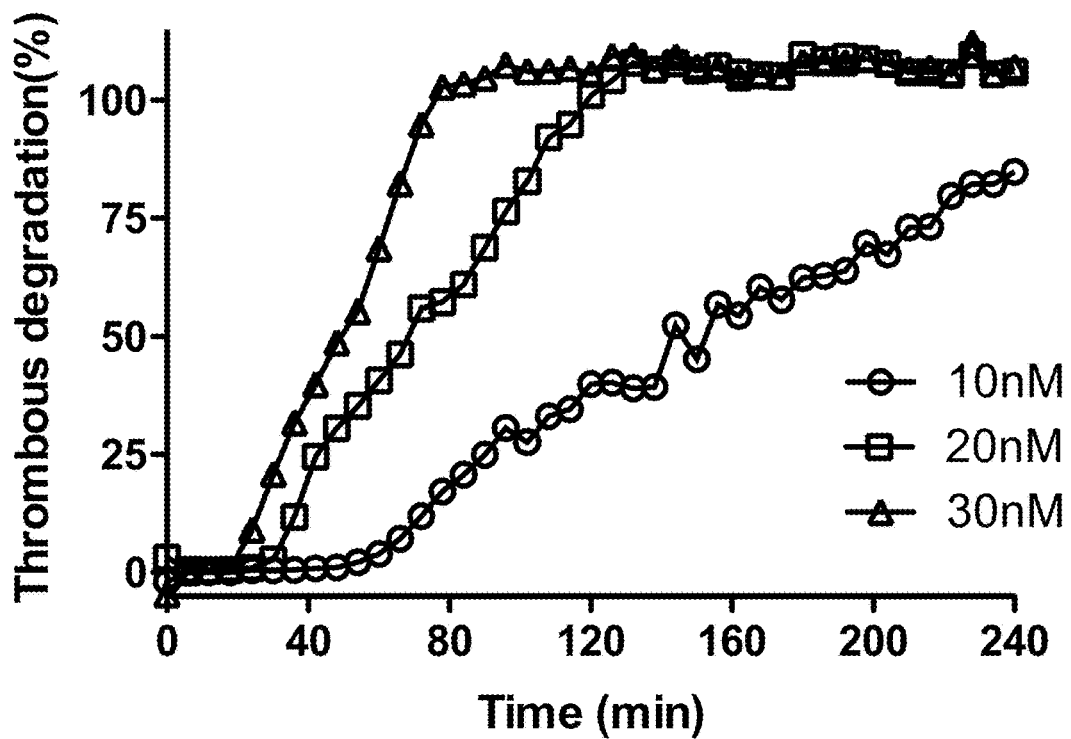

The results of thrombolytic assay summarized in FIG. 14B indicate that the present reteplase-(3D5 scFv) polypeptide, at the concentrations of 10 nM, 20 nM and 30 nM, can dissolves monkey clots in the human plasma.

Example 21: Human Fibrin Binding Affinities of Recombinant Reteplase-(3D5 scFv) Polypeptide and Alteplase To compare binding affinities of recombinant reteplase-(3D5 scFv) polypeptides and alteplase (ACTILYSE®, purchased from Boehringer Ingelheim) to human fibrin, ELISA analysis was performed and the procedure was similar to those described in preceding Examples. Briefly, human fibrinogen diluted with PBS was added to a 96-well polystyrene microplate at 100 µL/well, and the plate was then sealed and allowed to stand at 4° C., overnight.

Each fibrin plate was prepared as follows. 100 µL of TBS containing a final concentration of 1.0 U/mL thrombin (Sigma), 2 mM $CaCl_2$ and 7 mM L-cysteine (Merck) was added to the wells of the fibrinogen plate and incubated at 37° C. for 1 hour, which was then washed with TBS and blocked with the buffer (5% non-fat dry milk/PBS). Thereafter, 100 µL of reteplase-(3D5-scFv) or alteplase at a final concentration of 2, 20 or 200 nM were added to each well and incubated at room temperature for 1 hour. The plate was then washed three times, and them polyclonal rabbit HRP-conjugated anti-reteplase antibody diluted to 1/200 was added to the wells and incubated for 1 hour at room temperature. The wells were washed three times and added with 100 µL of TMB substrate buffer. 5 minutes later, the color development was stopped with 1 M HCl. The optical density (OD) was measured at 450 nm using a microplate reader.

Figure 15:
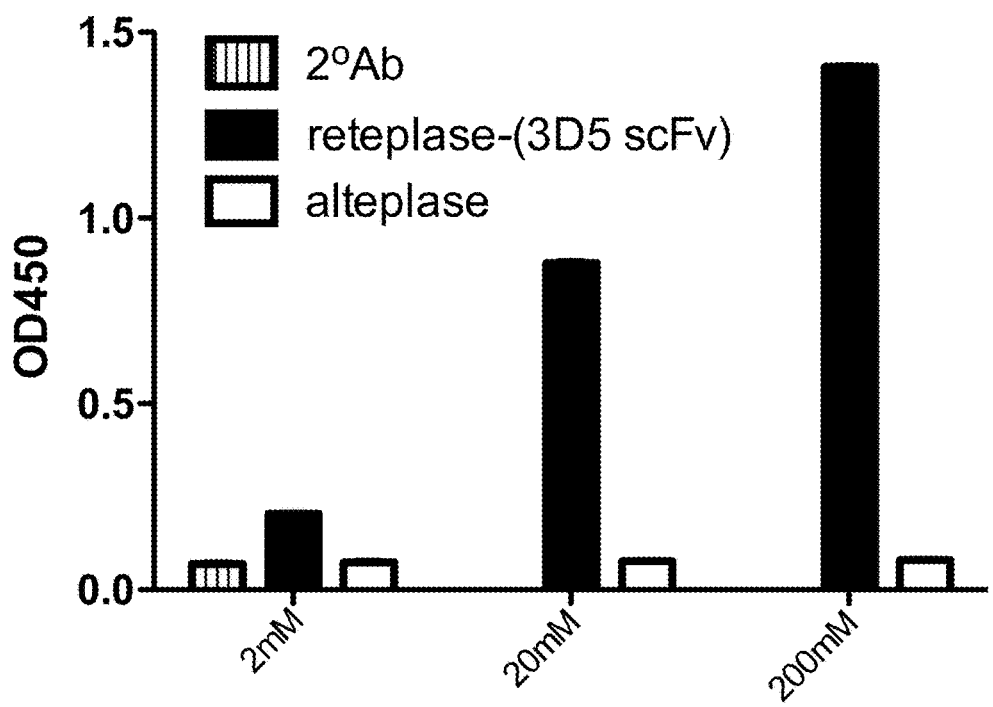
FIG. 15 is a bar diagram demonstrating the human fibrin binding affinities of reteplase-(3D5 scFv) and alteplase.

Recombinant reteplase-(3D5 scFv) polypeptide and alteplase were detected by polyclonal rabbit HRP-conjugated anti-reteplase antibody. The ELISA results summarized in FIG. 15 indicate that the reteplase-(3D5 scFv) polypeptides can bind specifically to human fibrin, and alteplase had no binding activity to human fibrin.

Example 22: Thrombolytic Activities of Recombinant Reteplase-(3D5 scFv) Polypeptide, Alteplase and Reteplase to Human Clot To compare thrombolytic activities of recombinant reteplase-(3D5 scFv) polypeptides, alteplase and reteplase to human clot, whole blood thrombolytic assay was performed and the procedure was similar as described in preceding Examples.

Reteplase-(3D5-scFv) polypeptide was diluted into 70 µL of PBS. The 70-µL samples were added simultaneously into the wells containing the monkey clots at room temperature for 3 minutes with a multichannel pipette. After removing samples, 70 µL of human plasma or PBS were added into the wells and the degradation of the human clots was determined using a microplate reader (Molecular Devices) by measuring the absorbance at 510 nm as the blood from the dissolved clot gradually covers the center of the well. The data were processed using Graph Pad Prism software.

Figure 16A:
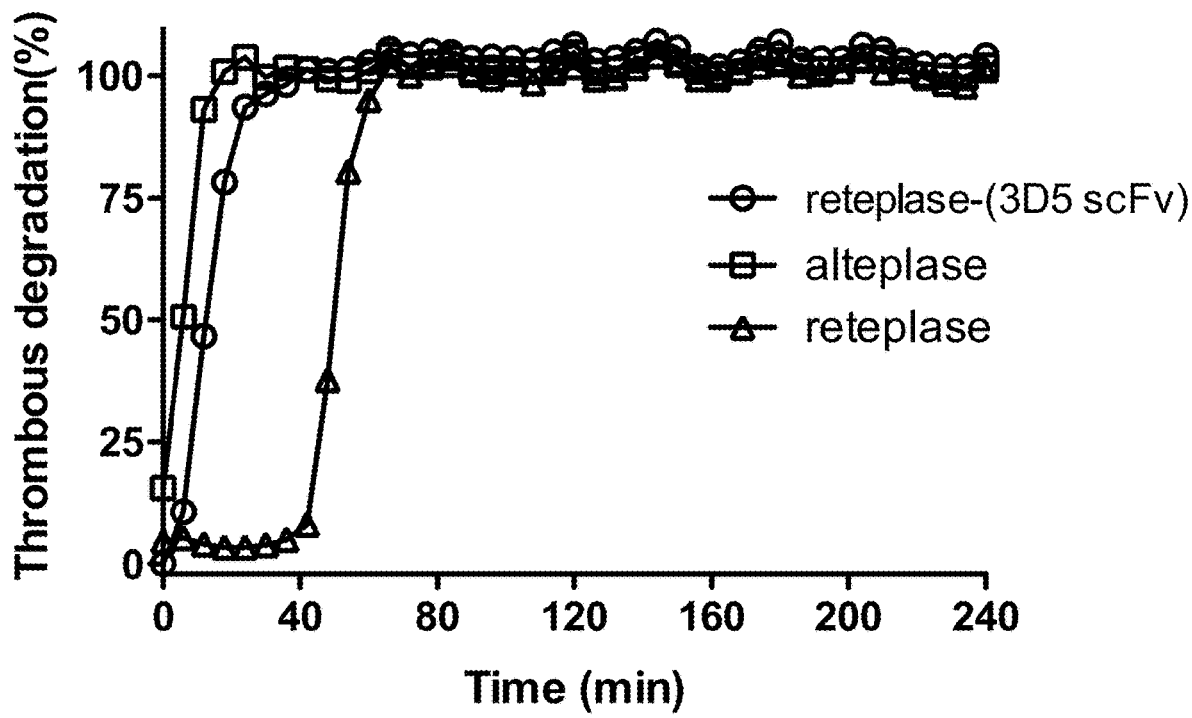
FIGS. 16A and 16B demonstrate the thrombolytic activity of reteplase-(3D5 scFv), reteplase and alteplase to human clots.
Figure 16B:
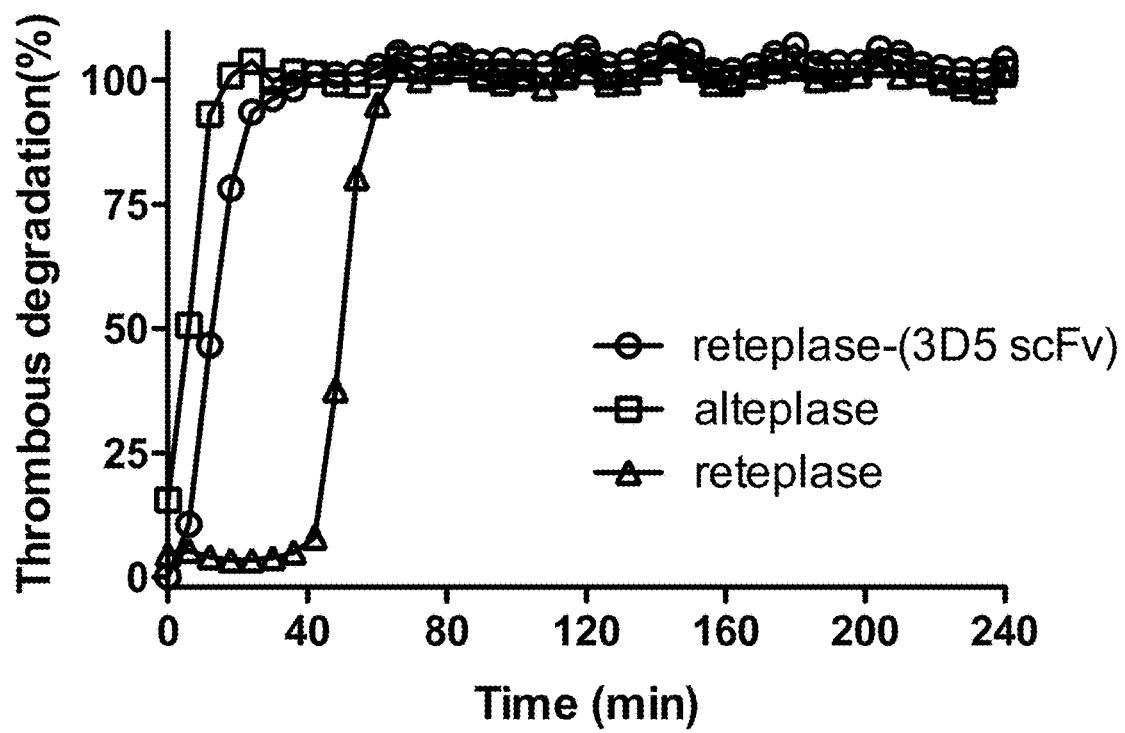

The results of thrombolytic assay summarized in FIG. 16A and FIG. 16B indicate that the reteplase-(3D5 scFv) polypeptide had a thrombolytic activity to human clot in PBS and human plasma, respectively.

Example 23: Kinetics of Proteolytic Activities of Recombinant Reteplase-(3D5 scFv) Polypeptide and Alteplase To investigate kinetics of proteolytic activities of reteplase-(3D5 scFv) polypeptide and alteplase, a chromogenic assay was performed by the conversion of plasminogen to plasmin catalyzed by recombinant reteplase-(3D5 scFv) polypeptide and alteplase. Briefly, the chromogenic substrate, $CH_3SO_2$-D-hexahydrotyrosine-Gly-Arg-p-nitroanilide·AcOH (Sigma), of various concentrations (0.1, 0.2, 0.4, 0.8, 1.6, 3.2 and 6.4 mM) and samples containing reteplase-(3D5 scFv) polypeptide or alteplase were incubated in 96-well flat-bottom plates (Nunc) at 25° C. for 15 minutes. The proteolytic activity of reteplase resulted in the hydrolysis of the substrate, and the release of free yellow-colored p-nitroaniline was measured at 405 nm using a plate reader.

Figure 17A:
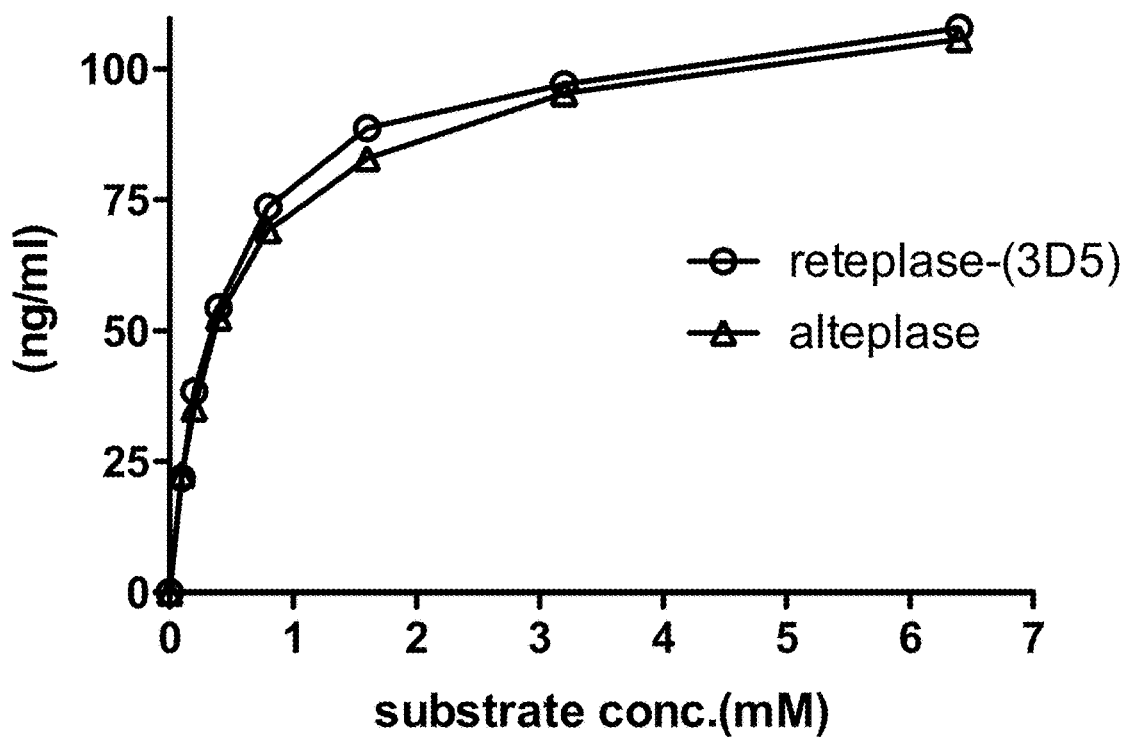
FIGS. 17A and 17B demonstrate the proteolytic activity of reteplase-(3D5 scFv) and alteplase.
Figure 17B:
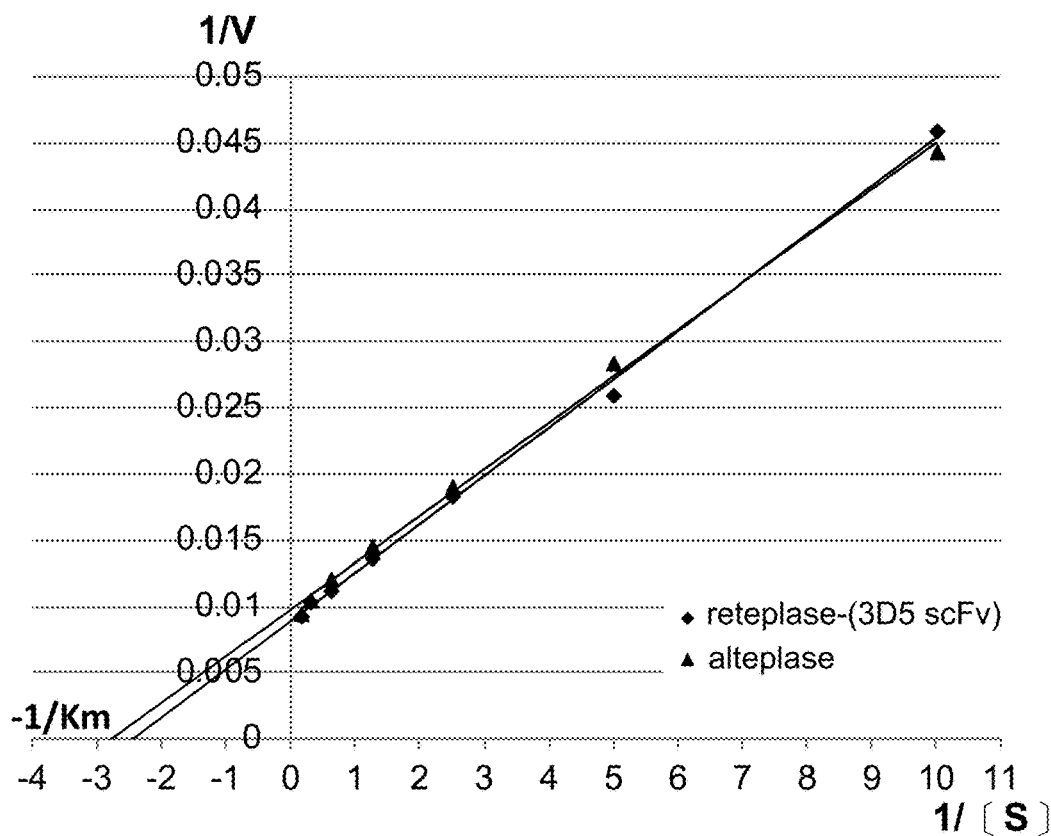

FIG. 17A is a line graph showing the proteolytic activity of the present recombinant reteplase-(3D5 scFv) polypeptide and alteplase at the designated substrate concentrations. FIG. 17B is a double-reciprocal plot (Lineweaver-Burk plot) made with data points derived from the data in FIG. 17A, and the [Km], [Vmax] and [Kcat] values of their protease activities can be then calculated from the Lineweaver-Burk plot. The [Km], [Vmax] and [Kcat] values of recombinant reteplase-(3D5 scFv) polypeptide are 0.41 mM, 170 nM/min and 0.85, respectively, whereas the [Km], [Vmax] and [Kcat] values of alteplase are 0.36 mM, 155 nM/min and 0.775, respectively. These data demonstrate that both reteplase-(3D5 scFv) polypeptide and alteplase have similar proteolytic activities to the chromogenic substrate.

Example 24: Stability Analysis of Recombinant Reteplase-(3D5 scFv) Polypeptide in Human Plasma To evaluate the stability of reteplase-(3D5 scFv) polypeptide in human plasma, the reteplase-(3D5 scFv) polypeptide was incubated in 10 or 20% human plasma for 3, 6, and 24 hours, and then ELISA analysis was carried out.

The fibrin-coated plate was prepared and the protocols were similar to those described in preceding Examples. Briefly, 96-well microplates were coated with human fibrinogen (Sigma) (20 µg/mL) in PBS buffer (100 µL/well). After overnight incubation at 4° C., the coated wells were washed with PBS buffer. To induce the cross-linking of human fibrin, coated wells was incubated at 37° C. for 1 hour with human α-thrombin (Sigma) at a final concentration of 1 U/mL in TBS buffer with 2 mM $CaCl_2$ and 7 mM L-cystine (Merck). After blocking the wells with a blocking buffer, 100 µL of reteplase-(3D5-scFv) polypeptide incubated in human plasma of 10% or 20% for 3, 6 and 24 hours were added respectively to each well and then the plates were incubated at room temperature for 1 hour. Thereafter, the plates were washed three times, and polyclonal rabbit HRP-conjugated anti-reteplase antibody diluted to 1/200 was added to the wells and incubated for 1 hour at room temperature. The wells were washed three times and added with 100 μL of TMB substrate buffer. 5 minutes later, the color development was stopped with 1 M HCl. The optical density (OD) was measured at 450 nm using a microplate reader (Molecular Devices) and the data were processed using Graph Pad Prism software.

Figure 18A:
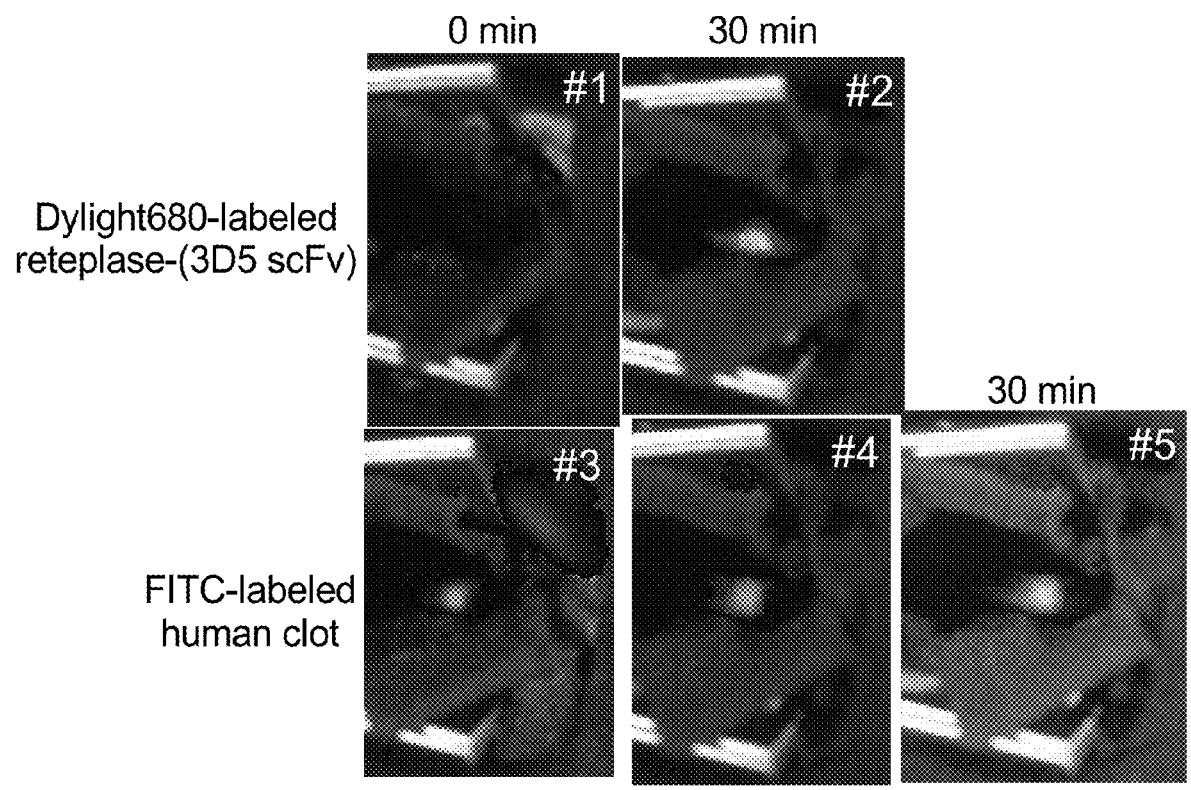
FIGS. 18A and 18B are IVIS images of mice treated with reteplase-(3D5 scFv) or reteplase.
Figure 18B:
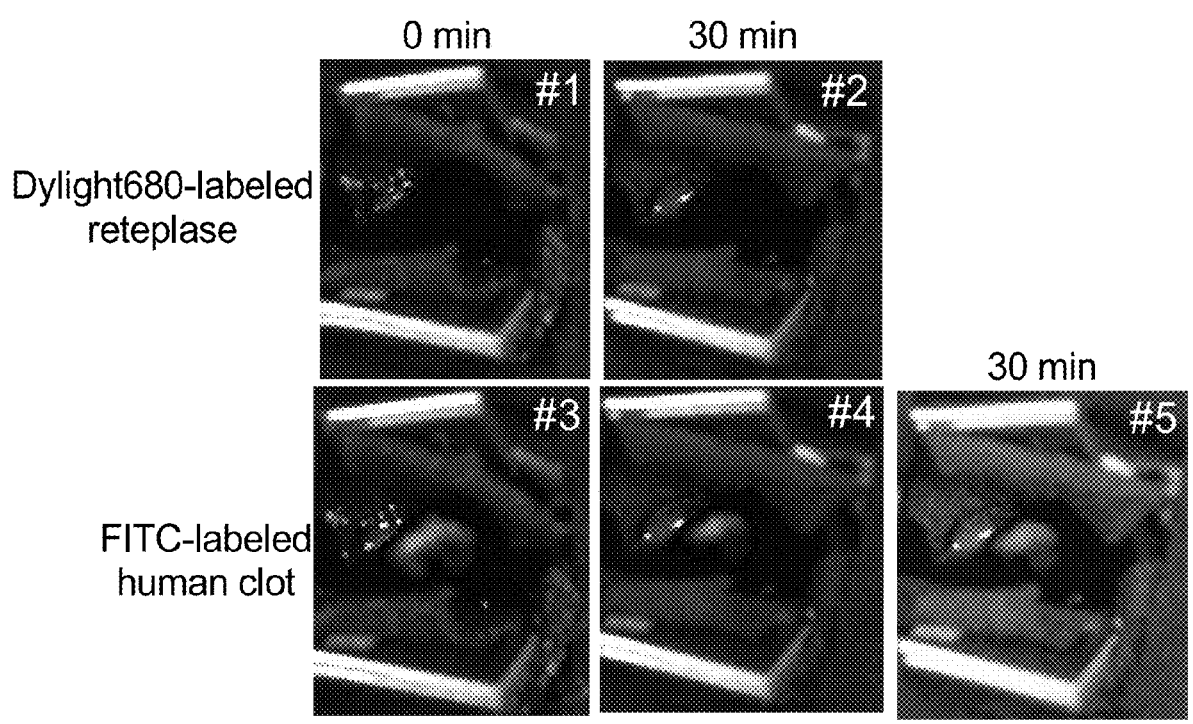
Figure 18C:
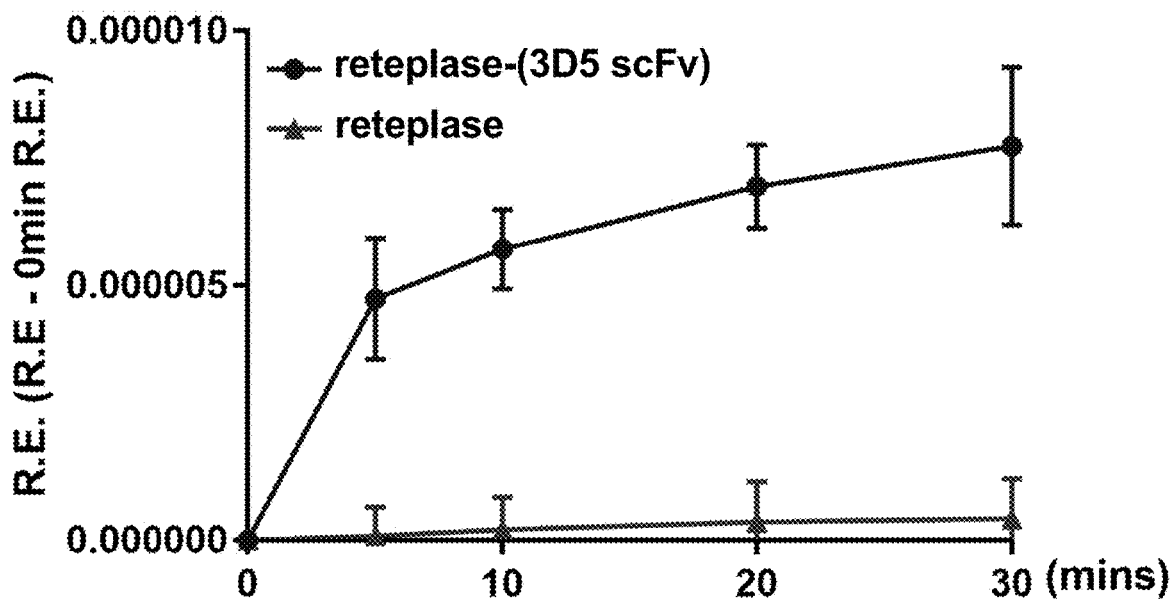
FIG. 18C is a line graph showing the targeting effect of reteplase-(3D5 scFv).

The ELISA results were summarized in FIG. 18, which indicate that the reteplase-(3D5 scFv) is stable in the presence of 10% or 20% human plasma.

Example 25: Targeting Effect of Recombinant Reteplase-(3D5 scFv) Polypeptide in Clot-Implanted Mouse Model To investigate the targeting effect of recombinant reteplase-(3D5 scFv) polypeptide in human clot-implanted mouse model, IVIS imaging analysis was performed. To monitor the implanted human clot in mouse model, FITC labeling kit (Thermo Scientific) was used to conjugate human clots before implanting the human clot into the blood vessel of the mouse according to the manufacturer's instructions. The FITC-labeled human clots were prepared in 384-well microplate (Axygen) to form adequate size of human clot for implanting into mouse inferior vena cava (IVC). Briefly, human fibrinogen was labeled with FITC dye at a final concentration of 1 mg/ml. The FITC-labeled fibrinogen was mixed with 4 μL of human blood. Then, the mixed blood sample was treated with thrombin (final conc. of $6.25 \times 10^{-3}$U) and calcium chloride at a final concentration of 67 mM in HEPES buffer (25 mM Hepes, 137 mM NaCl). Thereafter, 5 μL of the mixed blood samples were added to each well of 384-well microplate, and the plate was incubated at 37° C. for 1 hour to allow for the formation of human clots.

To monitor the location of the injected proteins, a Dylight 680 Antibody Labeling Kit (Thermo Scientific) was used to conjugate the recombinant reteplase-(3D5 scFv) polypeptide and reteplase before the treatment of recombinant reteplase-(3D5 scFv) polypeptide and reteplase, according to the manufacturer's instructions.

8 to 10-week-old NOD-SCID mice were purchased from Laboratory Animal Facility of Institute of Cellular and Organismic Biology, Academia Sinica (Taipei, Taiwan). FITC-labeled human clots were implanted into the mouse inferior vena cava (IVC). Briefly, mice were anaesthetized with isoflurane in $O_2$, and placed under a heat lamp to maintain the physiological body temperature. The abdominal wall was shaved and disinfected with 70% denatured ethanol. Median laparotomy was performed, and then the FITC-labeled human clot was placed into the IVC. The exposed IVC was observed in the IVIS Spectrum In Vivo Imaging System (PerkinElmer). Fluorescent images were captured with ex/em=459/520 (for detecting FITC) or ex/em=675/720 (for detecting Dylight680), using the Living Image Software V3.2. Images were captured at indicated time points using IVIS Spectrum imager and analyzed with Living Image software.

The mice were grouped into two mice per group, and were injected through orbital venous sinus with about 50 μL of 256 nM Dylight680-conjugated reteplase-(3D5 scFv) polypeptide (Group A) or reteplase (Group B). Fluorescent images from human clot-implanted mice were acquired at 0, 5, 10, 20 and 30 minutes after the administration of DyLight 680-conjugated proteins.

FIG. 18A shows five IVIS images of Group A mice, in which panel #1 and #2 were captured with ex/em=675/720, panel #3 and #4 were captured with ex/em=495/520, and the fluorescent signals in panel #2 and #4 were combined to give panel #5. The green fluorescence in both panel #3 and #4 indicates the presence of the FITC-labeled human clot in mice. On the other hand, right after the Dylight680-conjugated reteplase-(3D5 scFv) upon the injection of the polypeptide (0 minute), there were no significant red fluorescence in panel #1, whereas 30 minutes after the injection, intense red fluorescence was observed in panel #2. The overlapping red and green signals in the combined image in panel #5 indicates that the present Dylight680-conjugated reteplase-(3D5 scFv) polypeptide concentrates around the implanted human clot.

FIG. 18B shows five IVIS images of Group B mice, in which panel #1 and #2 were captured with ex/em=675/720, panel #3 and #4 were captured with ex/em=495/520, and the fluorescent signals in panel #2 and #4 were combined to give panel #5. Similar to the IVIS images in FIG. 18A, the green fluorescence in both panel #3 and #4 indicates the presence of the FITC-labeled human clot in mice. However, no red fluorescence was observed upon the administration of Dylight680-conjugated reteplase (panel #1) or 30 minutes after the administration (panel #2). The combined image in panel #5 indicates that no Dylight680-conjugated reteplase concentrates around the implanted human clot as there is only the green signal in the image.

To quantify the fluorescent level of Dylight680-labled samples in terms of radiant efficiency (R.E.), the fluorescence intensity of images captured at designated time points were normalized with respect to the reference image taken with ex/em=675/720 at 0 minute. Thus, the results were summarized in the FIG. 19C, which indicates that the present reteplase-(3D5 scFv) can target to the human clot in the IVC of mouse model, whereas reteplase cannot effectively target to the human clot in the IVC of mouse model.

Example 26: Half-Life of Recombinant Reteplase-(3D5 scFv) Polypeptide in Rat by ELISA To measure half-lives of alteplase, reteplase and recombinant reteplase-(3D5 scFv) polypeptide, ELISA assays were carried out in rat after i.v. administration. The protein levels of alteplase, reteplase and recombinant reteplase-(3D5 scFv) polypeptide in the serum samples were quantified using ELISA method. 6-week-old Wistar rat were purchased from BioLasco (Taipei, Taiwan). Rat were grouped into three rats per group, and were injected intravenously with about 500 μL of 0.364 mg/kg drug molecule.

For the ELISA assay, coated plates were prepared as follows. 100 μL of TBS containing a final concentration of 1.0 μg/ml polyclonal rabbit anti-reteplase antibody (produced by LTK BioLaboratories Co., Ltd., Taoyuan, Taiwan) was added to the wells of the plates, and the plates were then incubated at 4° C. for 18 hours, which was then washed with TBS and blocked with the buffer (5% non-fat dry milk/PBS).

Thereafter, 100 μL of collected blood samples under various dilution conditions were added to each well and incubated at room temperature for 1 hour. The plate was then washed three times; 100 μL of 1.65 μg/ml polyclonal rabbit HRP-conjugated with anti-reteplase antibody was added to the wells; and then the plate was incubated for 1 hour at room temperature. The wells were washed three times and added with 100 μL of TMB substrate buffer. 5 minutes later, the color development was stopped with 1 M HCl. The optical density (OD) was measured at 450 nm using a microplate reader.

Figure 19:
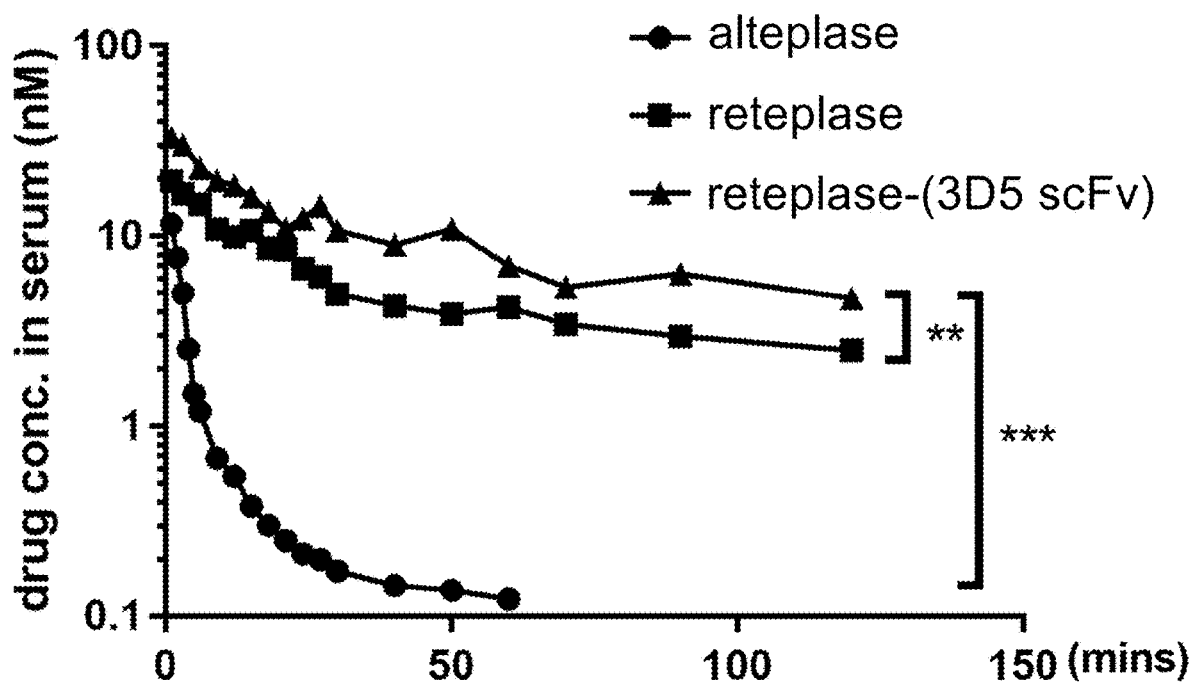
FIG. 19 shows the pharmacokinetic profiles of alteplase, reteplase and recombinant reteplase-(3D5 scFv) polypeptide.

FIG. 19 shows the pharmacokinetic profiles of alteplase, reteplase and recombinant reteplase-(3D5 scFv) polypeptide. As can be seen in FIG. 19, the present reteplase-(3D5 scFv) polypeptide exhibits higher protein levels in rat serum at various time points, compared with alteplase and reteplase. These data indicate that the present recombinant reteplase-(3D5 scFv) polypeptide has a longer half-life than alteplase or reteplase does.

Example 27: Half-Life of Recombinant Reteplase-(3D5 scFv) Polypeptide in Rat

To investigate the half-life of recombinant reteplase-(3D5 scFv) polypeptide, an additionally proteolytic assay was carried out in rat after i.v. administration. The serum level of the recombinant reteplase-(3D5 scFv) polypeptide was determined in terms of the proteolytic activity of reteplase-(3D5 scFv) polypeptide, and the protocols were similar to those described in preceding Examples.

6-week-old Wistar rat were purchased from BioLasco (Taipei, Taiwan). Rat were grouped into three mice per group, and were injected intravenously with about 500 µL of 0.364 mg/kg recombinant reteplase-(3D5 scFv) polypeptide or alteplase. Blood samples were collected at 10, 20, 40 and 120 minutes after i.v. administration.

0.8 mM of chromogenic substrate, $CH_3SO_2$-D-hexahydrotyrosine-Gly-Arg-p-nitroanilide·AcOH (Sigma) and each diluted blood samples (1/10) were incubated in 96-well flat-bottom plates (Nunc) at 25° C. for 15 minutes. The proteolytic activity of the present reteplase-(3D5 scFv) or alteplase resulted in the hydrolysis of the substrate, and the release of free yellow-colored p-nitroaniline was measured at 405 nm using a plate reader.

Figure 20:
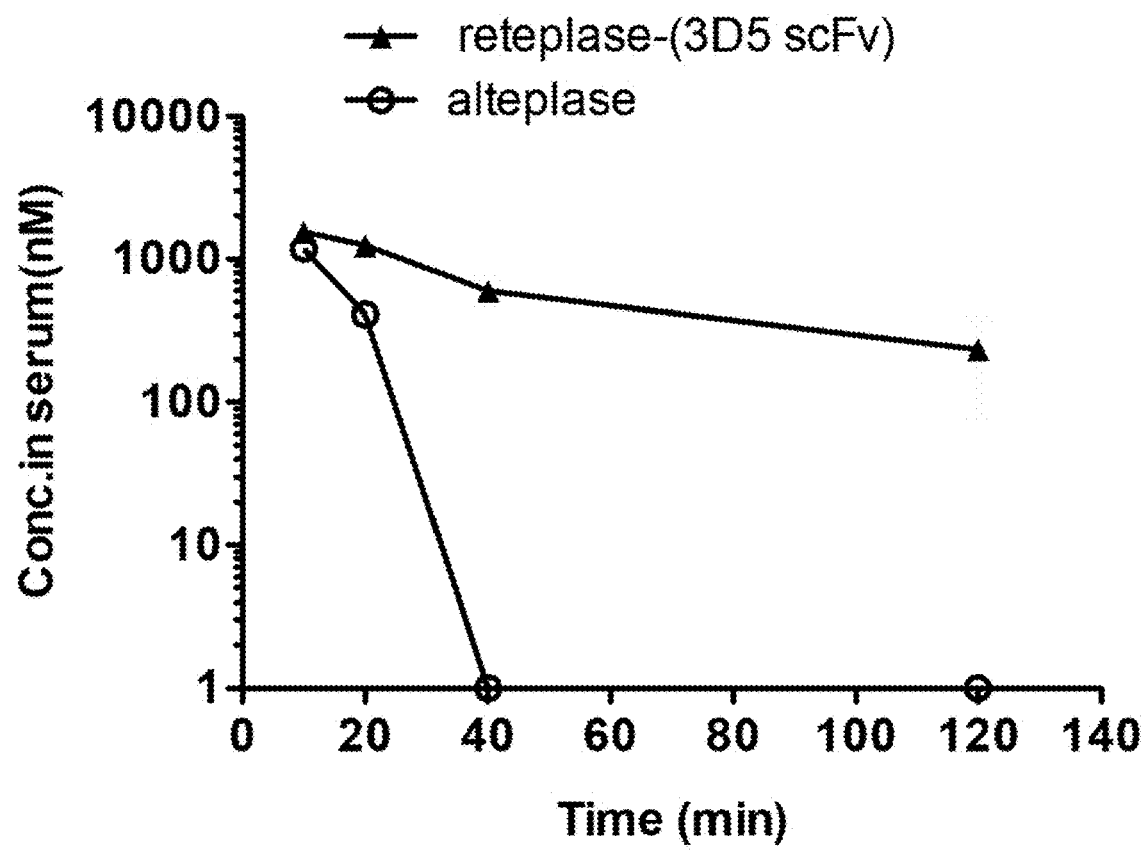
FIG. 20 shows the pharmacokinetic profiles of alteplase and recombinant reteplase-(3D5 scFv) polypeptide.

FIG. 20 shows the pharmacokinetic profiles of recombinant reteplase-(3D5 scFv) polypeptide and alteplase. As can be seen in FIG. 20, the present reteplase-(3D5 scFv) polypeptide exhibits significantly higher protein levels in rat serum, compared with alteplase does. In view of the foregoing, the present recombinant reteplase-(3D5 scFv) polypeptide has a longer half-life than alteplase does, which is in accord with the findings in previous Examples.

Example 28: Preparation of Recombinant (3D5 scFv)-Reteplase Polypeptide

The recombinant (3D5 $V_L$-(G4S)$_3$-$V_H$ scFv α fibrin)-reteplase polypeptide was configured by fusing 3D5 scFv specific for human fibrin to the N-terminus of reteplase through a flexible linker. The expression of the constructed gene in Expi293F cells and the purification of the expressed polypeptide were similar to those described in preceding Examples.

Figure 21A:
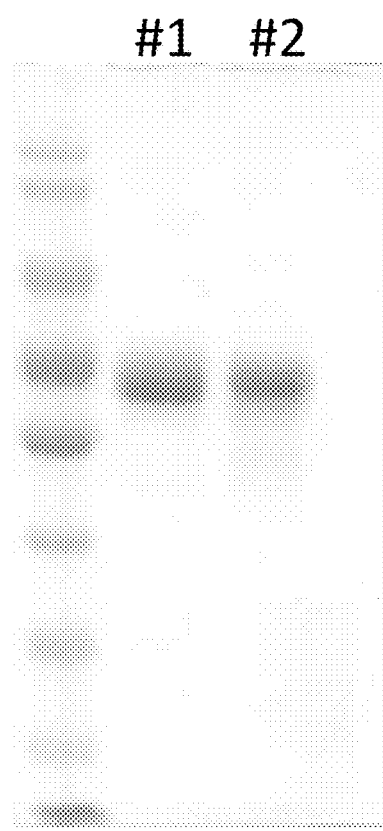
FIG. 21A shows the result of SDS-PAGE analysis of the purified recombinant (3D5 VL-(G4S)3-VH scFv α fibrin)-reteplase polypeptide.

The scFv had an orientation of $V_L$-linker-$V_H$, and the two domains were connected by a flexible linker. The sequence of the recombinant polypeptide is shown in SEQ ID NO: 14. Characterization of the new construct was carried out using SDS-PAGE. The 10% non-reducing SDA-PAGE results in FIG. 21A shows that the sample in #2 lane has an expected product with a molecular weight of about 71 kDa.

To compare binding affinities of recombinant (3D5 scFv)-reteplase polypeptides to human fibrinogen and fibrin, ELISA analysis was carried out, and the protocols were similar to those described in preceding Examples.

Figure 21B:
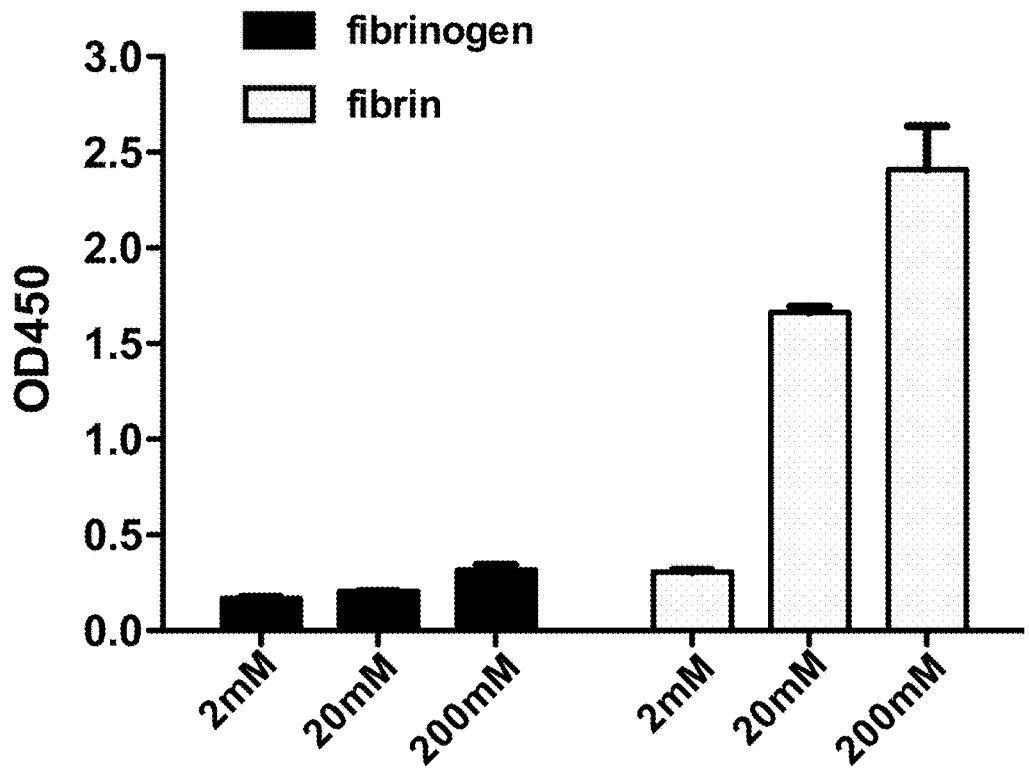
FIG. 21B shows the result of ELISA analysis of the binding of recombinant 3D5 VL-(G4S)3-VH scFv α fibrin)-reteplase polypeptide to human fibrin.

Recombinant (3D5 scFv)-reteplase polypeptide was detected using polyclonal rabbit HRP-conjugated with anti-reteplase antibody. The ELISA results summarized in FIG. 21B indicate that the present (3D5 scFv)-reteplase polypeptides can bind specifically to human fibrin but not to human fibrinogen.

Example 29: Dose-Dependent Thrombolytic Activities of Recombinant (3D5 scFv)-Reteplase Polypeptides to Human Clot To evaluate the thrombolytic activities of recombinant (3D5 scFv)-reteplase polypeptide to human clot, whole blood thrombolytic assay was performed and the protocols were similar to those described in preceding Examples.

Recombinant (3D5 scFv)-reteplase polypeptide was diluted into 70 µL of PBS at final concentrations of 12.5 nM, 25 nM and 50 nM. The 70-µL sample was added simultaneously into the wells containing the human clots at room temperature for 3 minutes with a multichannel pipette. After removing samples and washing the clot three times with 250 µL PBS, 70 µL of human serum was added into the wells and the degradation of the human clots was determined using a microplate reader (Molecular Devices) by measuring the absorbance at 510 nm as the blood from the dissolved clot gradually covers the center of the well. The data were processed using Graph Pad Prism software.

Figure 22:
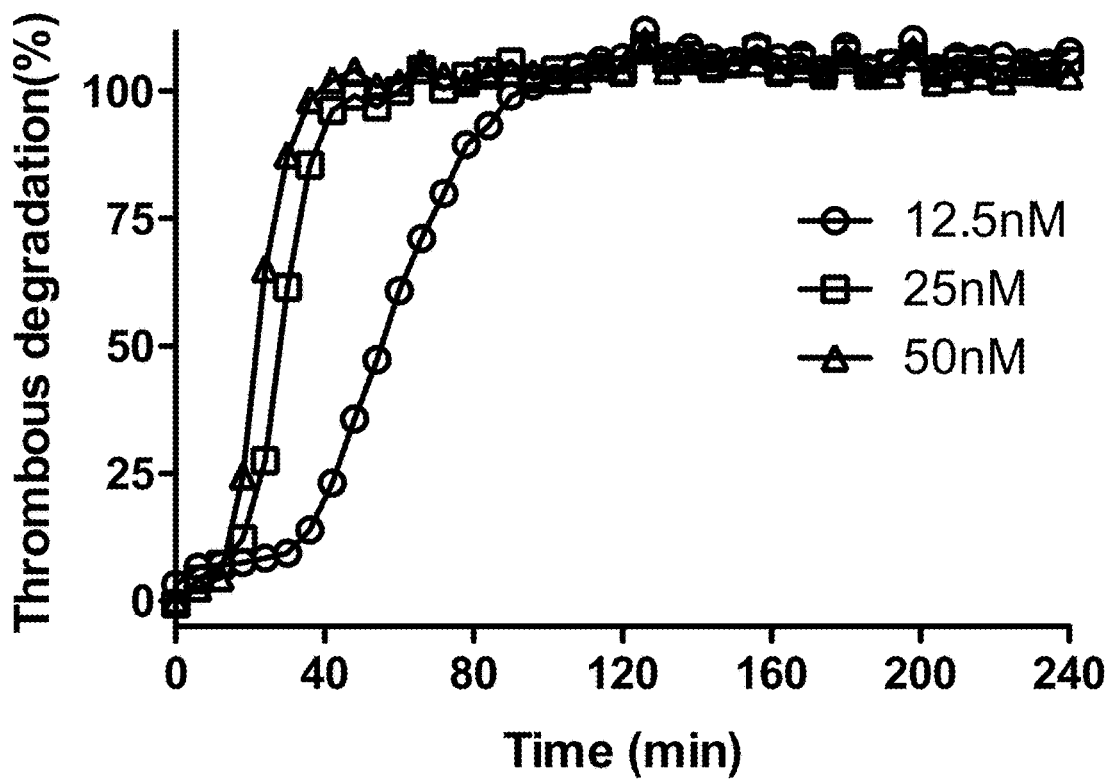
FIG. 22 shows the dose-dependent thrombolytic activities of recombinant (3D5 scFv)-reteplase polypeptides to human clot.

The results of the assay summarized in FIG. 22 indicate that the (3D5 scFv)-reteplase polypeptide targets to human clots and exhibits the thrombolytic activity at the concentrations of 12.5 nM, 25 nM and 50 nM.

It will be understood that the above description of embodiments is given by way of example only and that various modifications may be made by those with ordinary skill in the art. The above specification, examples, and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. An anti-fibrin antibody, wherein the anti-fibrin antibody binds to human fibrin with an affinity 10 times better than to human fibrinogen, wherein the anti-fibrin antibody comprises a light-chain variable domain and a heavy-chain variable domain, respectively having the amino acid sequence of, SEQ ID NOs: 1 and 2, SEQ ID NOs: 17 and 18, SEQ ID NOs: 19 and 20, or SEQ ID NOs: 21 and 22.

2. The anti-fibrin antibody according to claim 1, further comprising a linker having the sequence of SEQ ID NO: 16 connecting the light-chain variable domain and the heavy-chain variable domain of the anti-fibrin antibody.

3. The anti-fibrin antibody according to claim 1, wherein the anti-fibrin antibody comprises six complementarity-determining regions (CDRs) respectively having the amino acid sequences corresponding to residues 30 to 32 of SEQ ID NO: 1 (CDR-L1), residues 49 to 54 of SEQ ID NO: 1 (CDR-L2), residues 91 to 96 of SEQ ID NO: 1 (CDR-L3), residues 30 to 33 of SEQ ID NO: 2 (CDR-H1), residues 50 to 59 of SEQ ID NO: 2 (CDR-H2), and residues 98 to 106 of SEQ ID NO:2 (CDR-H3).

4. A polypeptide, comprising an anti-fibrin antibody and a serine protease moiety of human plasminogen activator (hu-tPA), wherein the anti-fibrin antibody binds to human fibrin with an affinity 10 times better than to human fibrinogen, wherein the anti-fibrin antibody comprises a light-chain variable domain and a heavy-chain variable domain, respectively having the amino acid sequence of, SEQ ID NOs: 1 and 2, SEQ ID NOs: 17 and 18, SEQ ID NOs: 19 and 20, or SEQ ID NOs: 21 and 22.

5. The polypeptide according to claim 4, wherein the serine protease moiety of hu-tPA is reteplase.

6. The polypeptide according to claim 4, wherein the polypeptide has a longer serum half-life in an animal than reteplase does.

7. The polypeptide according to claim 4, further comprising a linker disposed between the serine protease moiety of hu-tPA and the anti-fibrin antibody.

8. The polypeptide according to claim 4, further comprising a linker having the sequence of SEQ ID NO: 16 connecting the light-chain variable domain and the heavy-chain variable domain of the anti-fibrin antibody.

9. The polypeptide according to claim 4, wherein the polypeptide binds to human fibrin better than the hu-tPA does.

10. The polypeptide according to claim 4, wherein the polypeptide binds to human fibrin better than the hu-tPA does, and has a longer serum half-life in an animal than reteplase does.

11. The polypeptide according to claim 4, wherein the serine protease moiety of hu-tPA is linked to the N-terminus of the anti-fibrin antibody.

12. The polypeptide according to claim 11, wherein the polypeptide has the amino acid sequence of SEQ ID NO. 11 or 12.

13. The polypeptide according to claim 4, wherein the serine protease moiety of hu-tPA is linked to the C-terminus of the anti-fibrin antibody.

14. The polypeptide according to claim 13, wherein the polypeptide has the amino acid sequence of SEQ ID NO. 14.

15. A method for treating thrombosis in a subject in need thereof, comprising the step of administering to the subject an effective amount of a polypeptide according to claim 4.

* * * * *

SEQUENCE LISTING

<160> NUMBER OF SEQ ID NOS: 22

<210> SEQ ID NO 1
<211> LENGTH: 108
<212> TYPE: PRT
<213> ORGANISM: Artificial Sequence
<220> FEATURE:
<223> OTHER INFORMATION: Synthetic

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Asn Asn
            20                  25                  30

Val Ala Trp Tyr Gln Gln Lys Pro Gly Lys Ala Pro Lys Leu Leu Ile
        35                  40                  45

Phe Trp Ser Pro Trp Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Trp Asp Ser Pro Val
                85                  90                  95

Thr Phe Gly Gln Gly Thr Lys Val Glu Ile Lys Arg
            100                 105

<210> SEQ ID NO 2
<211> LENGTH: 118
<212> TYPE: PRT
<213> ORGANISM: Artificial Sequence
<220> FEATURE:
<223> OTHER INFORMATION: Synthetic

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Asp Phe
            20                  25                  30

Gly Ile His Trp Val Arg Gln Ala Pro Gly Lys Gly Leu Glu Trp Val
        35                  40                  45

Ala Ser Ile Trp Pro Ser Gly Gly Tyr Thr Tyr Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Trp Phe Tyr Ser Trp Tyr Asp Tyr Trp Gly Gln Gly Thr
            100                 105                 110

Leu Val Thr Val Ser Ser
        115

<210> SEQ ID NO 3
<211> LENGTH: 244
<212> TYPE: PRT
<213> ORGANISM: Artificial Sequence
<220> FEATURE:
<223> OTHER INFORMATION: Synthetic

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Asn Asn
            20                  25                  30

Val Ala Trp Tyr Gln Gln Lys Pro Gly Lys Ala Pro Lys Leu Leu Ile
        35                  40                  45

Phe Trp Ser Pro Trp Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Trp Asp Ser Pro Val
                 85                  90                  95

Thr Phe Gly Gln Gly Thr Lys Val Glu Ile Lys Arg Gly Ser Thr Ser
            100                 105                 110

Gly Ser Gly Lys Pro Gly Ser Gly Glu Gly Ser Thr Lys Gly Glu Val
        115                 120                 125

Gln Leu Val Glu Ser Gly Gly Gly Leu Val Gln Pro Gly Gly Ser Leu
    130                 135                 140

Arg Leu Ser Cys Ala Ala Ser Gly Phe Thr Ile Ser Asp Phe Gly Ile
145                 150                 155                 160

His Trp Val Arg Gln Ala Pro Gly Lys Gly Leu Glu Trp Val Ala Ser
                165                 170                 175

Ile Trp Pro Ser Gly Gly Tyr Thr Tyr Tyr Ala Asp Ser Val Lys Gly
            180                 185                 190

Arg Phe Thr Ile Ser Ala Asp Thr Ser Lys Asn Thr Ala Tyr Leu Gln
        195                 200                 205

Met Asn Ser Leu Arg Ala Glu Asp Thr Ala Val Tyr Tyr Cys Ala Arg
    210                 215                 220

Ser Trp Phe Tyr Ser Trp Tyr Asp Tyr Trp Gly Gln Gly Thr Leu Val
225                 230                 235                 240

Thr Val Ser Ser

<210> SEQ ID NO 4
<211> LENGTH: 244
<212> TYPE: PRT
<213> ORGANISM: Artificial Sequence
<220> FEATURE:
<223> OTHER INFORMATION: Synthetic

<400> SEQUENCE: 4

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Val Gly Phe Tyr
                 20                  25                  30

Val Ala Trp Tyr Gln Gln Lys Pro Gly Lys Ala Pro Lys Leu Leu Ile
             35                  40                  45

Ser Tyr Pro Ser Gly Leu Tyr Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Asp Tyr Pro Ile
                 85                  90                  95

Thr Phe Gly Gln Gly Thr Lys Val Glu Ile Lys Arg Gly Ser Thr Ser
            100                 105                 110

Gly Ser Gly Lys Pro Gly Ser Gly Glu Gly Ser Thr Lys Gly Glu Val
        115                 120                 125

Gln Leu Val Glu Ser Gly Gly Gly Leu Val Gln Pro Gly Gly Ser Leu
    130                 135                 140

Arg Leu Ser Cys Ala Ala Ser Gly Phe Thr Ile Asn Asp Phe Ser Ile
145                 150                 155                 160

His Trp Val Arg Gln Ala Pro Gly Lys Gly Leu Glu Trp Val Ala Gly
                165                 170                 175

Ile Trp Pro Tyr Gly Gly Tyr Thr Phe Tyr Ala Asp Ser Val Lys Gly

```
                    180                 185                 190
Arg Phe Thr Ile Ser Ala Asp Thr Ser Lys Asn Thr Ala Tyr Leu Arg
        195                 200                 205

Met Asn Ser Leu Arg Ala Glu Asp Thr Ala Val Tyr Tyr Cys Ala Arg
    210                 215                 220

Phe Gly Tyr Tyr Ser Phe Gly Asp Tyr Trp Gly Gln Gly Thr Leu Val
225                 230                 235                 240

Thr Val Ser Ser

<210> SEQ ID NO 5
<211> LENGTH: 241
<212> TYPE: PRT
<213> ORGANISM: Artificial Sequence
<220> FEATURE:
<223> OTHER INFORMATION: Synthetic

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Asn Asn
            20                  25                  30

Val Ala Trp Tyr Gln Gln Lys Pro Gly Lys Ala Pro Lys Leu Leu Ile
        35                  40                  45

Phe Trp Ser Pro Trp Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Trp Asp Ser Pro Val
                85                  90                  95

Thr Phe Gly Gln Gly Thr Lys Val Glu Ile Lys Arg Gly Gly Gly Gly
            100                 105                 110

Ser Gly Gly Gly Gly Ser Gly Gly Gly Ser Glu Val Gln Leu Val
        115                 120                 125

Glu Ser Gly Gly Gly Leu Val Gln Pro Gly Gly Ser Leu Arg Leu Ser
130                 135                 140

Cys Ala Ala Ser Gly Phe Thr Ile Ser Asp Phe Gly Ile His Trp Val
145                 150                 155                 160

Arg Gln Ala Pro Gly Lys Gly Leu Glu Trp Val Ala Ser Ile Trp Pro
                165                 170                 175

Ser Gly Gly Tyr Thr Tyr Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ala Arg Ser Trp Phe
    210                 215                 220

Tyr Ser Trp Tyr Asp Tyr Trp Gly Gln Gly Thr Leu Val Thr Val Ser
225                 230                 235                 240

Ser

<210> SEQ ID NO 6
<211> LENGTH: 214
<212> TYPE: PRT
<213> ORGANISM: Artificial Sequence
<220> FEATURE:
<223> OTHER INFORMATION: Synthetic

<400> SEQUENCE: 6
```

```
Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Tyr
            20                  25                  30

Ile Ala Trp Phe Gln His Lys Pro Gly Lys Gly Pro Arg Leu Leu Ile
            35                  40                  45

His Tyr Thr Ser Thr Leu Gln Pro Gly Ile Pro Ser Arg Phe Ser Gly
    50                  55                  60

Ser Gly Ser Gly Arg Asp Tyr Ser Phe Ser Ile Ser Asn Leu Glu Pro
65              70                  75                  80

Glu Asp Leu Ala Thr Tyr Tyr Cys Leu Gln Tyr Asp Asn Leu Thr Trp
                85                  90                  95

Thr Phe Gly Gly Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
            210

<210> SEQ ID NO 7
<211> LENGTH: 443
<212> TYPE: PRT
<213> ORGANISM: Artificial Sequence
<220> FEATURE:
<223> OTHER INFORMATION: Synthetic

<400> SEQUENCE: 7

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
            35                  40                  45

Gly Trp Ile Asn Thr Tyr Thr Gly Glu Ala Thr Tyr Ala Asp Asp Phe
    50                  55                  60

Lys Gly Arg Phe Ala Phe Ser Leu Glu Thr Ser Ala Asn Thr Ala Tyr
65              70                  75                  80

Val Gln Ile Asn Asn Leu Lys Asn Glu Asp Thr Ala Thr Tyr Phe Cys
                85                  90                  95

Ala Arg Leu Met Asp Tyr Trp Gly Gln Gly Thr Ser Val Thr Val Ser
                100                 105                 110

Ser Ala Ser Thr Lys Gly Pro Ser Val Phe Pro Leu Ala Pro Ser Ser
            115                 120                 125

Lys Ser Thr Ser Gly Gly Thr Ala Ala Leu Gly Cys Leu Val Lys Asp
130                 135                 140
```

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
            165                 170                 175

Ser Leu Ser Ser Val Val Thr Val Pro Ser Ser Ser Leu Gly Thr Gln
        180                 185                 190

Thr Tyr Ile Cys Asn Val Asn His Lys Pro Ser Asn Thr Lys Val Asp
        195                 200                 205

Lys Lys Ala Glu Pro Lys Ser Cys Asp Lys Thr His Thr Cys Pro Pro
210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
            245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
290                 295                 300

Leu His Gln Asp Trp Leu Asn Gly Lys Asp Tyr Lys Cys Lys Val Ser
305                 310                 315                 320

Asn Lys Ala Leu Pro Ala Pro Ile Glu Lys Thr Ile Ser Lys Ala Lys
            325                 330                 335

Gly Gln Pro Arg Glu Pro Gln Val Tyr Thr Leu Pro Pro Ser Arg Asp
        340                 345                 350

Glu Leu Thr Arg Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
            405                 410                 415

Asn Val Phe Ser Cys Ser Val Met His Glu Ala Leu His Asn His Tyr
        420                 425                 430

Thr Gln Lys Ser Leu Ser Leu Ser Pro Gly Lys
        435                 440

<210> SEQ ID NO 8
<211> LENGTH: 214
<212> TYPE: PRT
<213> ORGANISM: Artificial Sequence
<220> FEATURE:
<223> OTHER INFORMATION: Synthetic

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Asn Asn
            20                  25                  30

Val Ala Trp Tyr Gln Gln Lys Pro Gly Lys Ala Pro Lys Leu Leu Ile
        35                  40                  45

Phe Trp Ser Pro Trp Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Trp Asp Ser Pro Val
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 9
<211> LENGTH: 448
<212> TYPE: PRT
<213> ORGANISM: Artificial Sequence
<220> FEATURE:
<223> OTHER INFORMATION: Synthetic

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Asp Phe
            20                  25                  30

Gly Ile His Trp Val Arg Gln Ala Pro Gly Lys Gly Leu Glu Trp Val
        35                  40                  45

Ala Ser Ile Trp Pro Ser Gly Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Trp Phe Tyr Ser Trp Tyr Asp Tyr Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Ala Glu Pro Lys Ser Cys Asp Lys Thr
    210             215                 220

His Thr Cys Pro Pro Cys Pro Ala Pro Glu Leu Leu Gly Gly Pro Ser
225             230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Asp Tyr
305             310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
        340                 345                 350

Pro Pro Ser Arg Asp Glu Leu Thr Arg Asn Gln Val Ser Leu Thr Cys
    355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385             390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly Lys
    435                 440                 445

<210> SEQ ID NO 10
<211> LENGTH: 611
<212> TYPE: PRT
<213> ORGANISM: Artificial Sequence
<220> FEATURE:
<223> OTHER INFORMATION: Synthetic

<400> SEQUENCE: 10

Ser Tyr Gln Gly Asn Ser Asp Cys Tyr Phe Gly Asn Gly Ser Ala Tyr
1               5                   10                  15

Arg Gly Thr His Ser Leu Thr Glu Ser Gly Ala Ser Cys Leu Pro Trp
            20                  25                  30

Asn Ser Met Ile Leu Ile Gly Lys Val Tyr Thr Ala Gln Asn Pro Ser
        35                  40                  45

Ala Gln Ala Leu Gly Leu Gly Lys His Asn Tyr Cys Arg Asn Pro Asp
    50                  55                  60

Gly Asp Ala Lys Pro Trp Cys His Val Leu Lys Asn Arg Arg Leu Thr
65              70                  75                  80

Trp Glu Tyr Cys Asp Val Pro Ser Cys Ser Thr Cys Gly Leu Arg Gln
            85                  90                  95

Tyr Ser Gln Pro Gln Phe Arg Ile Lys Gly Gly Leu Phe Ala Asp Ile
            100                 105                 110

Ala Ser His Pro Trp Gln Ala Ala Ile Phe Ala Lys His Arg Arg Ser
        115                 120                 125

-continued

```
Pro Gly Glu Arg Phe Leu Cys Gly Gly Ile Leu Ile Ser Ser Cys Trp
    130                 135                 140
Ile Leu Ser Ala Ala His Cys Phe Gln Glu Arg Phe Pro Pro His His
145                 150                 155                 160
Leu Thr Val Ile Leu Gly Arg Thr Tyr Arg Val Val Pro Gly Glu Glu
                165                 170                 175
Glu Gln Lys Phe Glu Val Glu Lys Tyr Ile Val His Lys Glu Phe Asp
            180                 185                 190
Asp Asp Thr Tyr Asp Asn Asp Ile Ala Leu Leu Gln Leu Lys Ser Asp
        195                 200                 205
Ser Ser Arg Cys Ala Gln Glu Ser Ser Val Val Arg Thr Val Cys Leu
    210                 215                 220
Pro Pro Ala Asp Leu Gln Leu Pro Asp Trp Thr Glu Cys Glu Leu Ser
225                 230                 235                 240
Gly Tyr Gly Lys His Glu Ala Leu Ser Pro Phe Tyr Ser Glu Arg Leu
                245                 250                 255
Lys Glu Ala His Val Arg Leu Tyr Pro Ser Ser Arg Cys Thr Ser Gln
            260                 265                 270
His Leu Leu Asn Arg Thr Val Thr Asp Asn Met Leu Cys Ala Gly Asp
        275                 280                 285
Thr Arg Ser Gly Gly Pro Gln Ala Asn Leu His Asp Ala Cys Gln Gly
    290                 295                 300
Asp Ser Gly Gly Pro Leu Val Cys Leu Asn Asp Gly Arg Met Thr Leu
305                 310                 315                 320
Val Gly Ile Ile Ser Trp Gly Leu Gly Cys Gly Gln Lys Asp Val Pro
                325                 330                 335
Gly Val Tyr Thr Lys Val Thr Asn Tyr Leu Asp Trp Ile Arg Asp Asn
            340                 345                 350
Met Arg Pro Ala Ser Gly Gly Gly Ser Gly Gly Gly Ser Gly
        355                 360                 365
Gly Gly Gly Ser Asp Ile Gln Met Thr Gln Ser Pro Ser Ser Leu Ser
    370                 375                 380
Ala Ser Leu Gly Gly Lys Val Thr Ile Thr Cys Lys Ala Ser Gln Asp
385                 390                 395                 400
Ile Asn Lys Tyr Ile Ala Trp Phe Gln His Lys Pro Gly Lys Gly Pro
                405                 410                 415
Arg Leu Leu Ile His Tyr Thr Ser Thr Leu Gln Pro Gly Ile Pro Ser
            420                 425                 430
Arg Phe Ser Gly Ser Gly Ser Gly Arg Asp Tyr Ser Phe Ser Ile Ser
        435                 440                 445
Asn Leu Glu Pro Glu Asp Leu Ala Thr Tyr Tyr Cys Leu Gln Tyr Asp
    450                 455                 460
Asn Leu Thr Trp Thr Phe Gly Gly Gly Thr Lys Leu Glu Ile Lys Arg
465                 470                 475                 480
Gly Ser Thr Ser Gly Ser Gly Lys Pro Gly Ser Gly Glu Gly Ser Thr
                485                 490                 495
Lys Gly Gln Ile Gln Leu Val Gln Ser Gly Pro Glu Leu Lys Lys Pro
            500                 505                 510
Gly Glu Thr Val Lys Ile Ser Cys Lys Ala Ser Gly Tyr Thr Phe Thr
        515                 520                 525
Asn Tyr Gly Met Asn Trp Val Lys Gln Ala Pro Gly Lys Gly Leu Lys
    530                 535                 540
```

Trp Met Gly Trp Ile Asn Thr Tyr Thr Gly Glu Ala Thr Tyr Ala Asp
545                 550                 555                 560

Asp Phe Lys Gly Arg Phe Ala Phe Ser Leu Glu Thr Ser Ala Asn Thr
                565                 570                 575

Ala Tyr Val Gln Ile Asn Asn Leu Lys Asn Glu Asp Thr Ala Thr Tyr
            580                 585                 590

Phe Cys Ala Arg Leu Met Asp Tyr Trp Gly Gln Gly Thr Ser Val Thr
        595                 600                 605

Val Ser Ser
    610

<210> SEQ ID NO 11
<211> LENGTH: 613
<212> TYPE: PRT
<213> ORGANISM: Artificial Sequence
<220> FEATURE:
<223> OTHER INFORMATION: Synthetic

<400> SEQUENCE: 11

Ser Tyr Gln Gly Asn Ser Asp Cys Tyr Phe Gly Asn Gly Ser Ala Tyr
1               5                   10                  15

Arg Gly Thr His Ser Leu Thr Glu Ser Gly Ala Ser Cys Leu Pro Trp
            20                  25                  30

Asn Ser Met Ile Leu Ile Gly Lys Val Tyr Thr Ala Gln Asn Pro Ser
        35                  40                  45

Ala Gln Ala Leu Gly Leu Gly Lys His Asn Tyr Cys Arg Asn Pro Asp
    50                  55                  60

Gly Asp Ala Lys Pro Trp Cys His Val Leu Lys Asn Arg Arg Leu Thr
65                  70                  75                  80

Trp Glu Tyr Cys Asp Val Pro Ser Cys Ser Thr Cys Gly Leu Arg Gln
                85                  90                  95

Tyr Ser Gln Pro Gln Phe Arg Ile Lys Gly Gly Leu Phe Ala Asp Ile
            100                 105                 110

Ala Ser His Pro Trp Gln Ala Ala Ile Phe Ala Lys His Arg Arg Ser
        115                 120                 125

Pro Gly Glu Arg Phe Leu Cys Gly Gly Ile Leu Ile Ser Ser Cys Trp
    130                 135                 140

Ile Leu Ser Ala Ala His Cys Phe Gln Glu Arg Phe Pro Pro His His
145                 150                 155                 160

Leu Thr Val Ile Leu Gly Arg Thr Tyr Arg Val Val Pro Gly Glu Glu
                165                 170                 175

Glu Gln Lys Phe Glu Val Glu Lys Tyr Ile Val His Lys Glu Phe Asp
            180                 185                 190

Asp Asp Thr Tyr Asp Asn Asp Ile Ala Leu Leu Gln Leu Lys Ser Asp
        195                 200                 205

Ser Ser Arg Cys Ala Gln Glu Ser Ser Val Val Arg Thr Val Cys Leu
    210                 215                 220

Pro Pro Ala Asp Leu Gln Leu Pro Asp Trp Thr Glu Cys Glu Leu Ser
225                 230                 235                 240

Gly Tyr Gly Lys His Glu Ala Leu Ser Pro Phe Tyr Ser Glu Arg Leu
                245                 250                 255

Lys Glu Ala His Val Arg Leu Tyr Pro Ser Ser Arg Cys Thr Ser Gln
            260                 265                 270

His Leu Leu Asn Arg Thr Val Thr Asp Asn Met Leu Cys Ala Gly Asp
        275                 280                 285

```
Thr Arg Ser Gly Gly Pro Gln Ala Asn Leu His Asp Ala Cys Gln Gly
    290                 295                 300

Asp Ser Gly Gly Pro Leu Val Cys Leu Asn Asp Gly Arg Met Thr Leu
305                 310                 315                 320

Val Gly Ile Ile Ser Trp Gly Leu Gly Cys Gly Gln Lys Asp Val Pro
                325                 330                 335

Gly Val Tyr Thr Lys Val Thr Asn Tyr Leu Asp Trp Ile Arg Asp Asn
            340                 345                 350

Met Arg Pro Ala Ser Gly Gly Gly Ser Gly Gly Gly Ser Gly
        355                 360                 365

Gly Gly Gly Ser Asp Ile Gln Met Thr Gln Ser Pro Ser Ser Leu Ser
370                 375                 380

Ala Ser Val Gly Asp Arg Val Thr Ile Thr Cys Arg Ala Ser Gln Asp
385                 390                 395                 400

Val Ser Asn Asn Val Ala Trp Tyr Gln Gln Lys Pro Gly Lys Ala Pro
                405                 410                 415

Lys Leu Leu Ile Phe Trp Ser Pro Trp Leu Tyr Ser Gly Val Pro Ser
            420                 425                 430

Arg Phe Ser Gly Ser Gly Ser Gly Thr Asp Phe Thr Leu Thr Ile Ser
        435                 440                 445

Ser Leu Gln Pro Glu Asp Phe Ala Thr Tyr Tyr Cys Gln Gln Gly Trp
450                 455                 460

Asp Ser Pro Val Thr Phe Gly Gln Gly Thr Lys Val Glu Ile Lys Arg
465                 470                 475                 480

Gly Gly Gly Gly Ser Gly Gly Gly Ser Gly Gly Gly Gly Ser Glu
                485                 490                 495

Val Gln Leu Val Glu Ser Gly Gly Gly Leu Val Gln Pro Gly Gly Ser
            500                 505                 510

Leu Arg Leu Ser Cys Ala Ala Ser Gly Phe Thr Ile Ser Asp Phe Gly
        515                 520                 525

Ile His Trp Val Arg Gln Ala Pro Gly Lys Gly Leu Glu Trp Val Ala
    530                 535                 540

Ser Ile Trp Pro Ser Gly Gly Tyr Thr Tyr Tyr Ala Asp Ser Val Lys
545                 550                 555                 560

Gly Arg Phe Thr Ile Ser Ala Asp Thr Ser Lys Asn Thr Ala Tyr Leu
                565                 570                 575

Gln Met Asn Ser Leu Arg Ala Glu Asp Thr Ala Val Tyr Tyr Cys Ala
            580                 585                 590

Arg Ser Trp Phe Tyr Ser Trp Tyr Asp Tyr Trp Gly Gln Gly Thr Leu
        595                 600                 605

Val Thr Val Ser Ser
    610

<210> SEQ ID NO 12
<211> LENGTH: 616
<212> TYPE: PRT
<213> ORGANISM: Artificial Sequence
<220> FEATURE:
<223> OTHER INFORMATION: Synthetic

<400> SEQUENCE: 12

Ser Tyr Gln Gly Asn Ser Asp Cys Tyr Phe Gly Asn Gly Ser Ala Tyr
1               5                   10                  15

Arg Gly Thr His Ser Leu Thr Glu Ser Gly Ala Ser Cys Leu Pro Trp
            20                  25                  30
```

```
Asn Ser Met Ile Leu Ile Gly Lys Val Tyr Thr Ala Gln Asn Pro Ser
         35                  40                  45

Ala Gln Ala Leu Gly Leu Gly Lys His Asn Tyr Cys Arg Asn Pro Asp
 50                  55                  60

Gly Asp Ala Lys Pro Trp Cys His Val Leu Lys Asn Arg Arg Leu Thr
 65                  70                  75                  80

Trp Glu Tyr Cys Asp Val Pro Ser Cys Ser Thr Cys Gly Leu Arg Gln
                 85                  90                  95

Tyr Ser Gln Pro Gln Phe Arg Ile Lys Gly Gly Leu Phe Ala Asp Ile
            100                 105                 110

Ala Ser His Pro Trp Gln Ala Ala Ile Phe Ala Lys His Arg Arg Ser
            115                 120                 125

Pro Gly Glu Arg Phe Leu Cys Gly Gly Ile Leu Ile Ser Ser Cys Trp
            130                 135                 140

Ile Leu Ser Ala Ala His Cys Phe Gln Glu Arg Phe Pro Pro His His
145                 150                 155                 160

Leu Thr Val Ile Leu Gly Arg Thr Tyr Arg Val Val Pro Gly Glu Glu
                165                 170                 175

Glu Gln Lys Phe Glu Val Glu Lys Tyr Ile Val His Lys Glu Phe Asp
            180                 185                 190

Asp Asp Thr Tyr Asp Asn Asp Ile Ala Leu Leu Gln Leu Lys Ser Asp
            195                 200                 205

Ser Ser Arg Cys Ala Gln Glu Ser Ser Val Val Arg Thr Val Cys Leu
            210                 215                 220

Pro Pro Ala Asp Leu Gln Leu Pro Asp Trp Thr Glu Cys Glu Leu Ser
225                 230                 235                 240

Gly Tyr Gly Lys His Glu Ala Leu Ser Pro Phe Tyr Ser Glu Arg Leu
                245                 250                 255

Lys Glu Ala His Val Arg Leu Tyr Pro Ser Ser Arg Cys Thr Ser Gln
            260                 265                 270

His Leu Leu Asn Arg Thr Val Thr Asp Asn Met Leu Cys Ala Gly Asp
            275                 280                 285

Thr Arg Ser Gly Gly Pro Gln Ala Asn Leu His Asp Ala Cys Gln Gly
290                 295                 300

Asp Ser Gly Gly Pro Leu Val Cys Leu Asn Asp Gly Arg Met Thr Leu
305                 310                 315                 320

Val Gly Ile Ile Ser Trp Gly Leu Gly Cys Gly Gln Lys Asp Val Pro
                325                 330                 335

Gly Val Tyr Thr Lys Val Thr Asn Tyr Leu Asp Trp Ile Arg Asp Asn
            340                 345                 350

Met Arg Pro Ala Ser Gly Gly Gly Ser Gly Gly Gly Ser Gly
            355                 360                 365

Gly Gly Gly Ser Asp Ile Gln Met Thr Gln Ser Pro Ser Ser Leu Ser
            370                 375                 380

Ala Ser Val Gly Asp Arg Val Thr Ile Thr Cys Arg Ala Ser Gln Asp
385                 390                 395                 400

Val Ser Asn Asn Val Ala Trp Tyr Gln Gln Lys Pro Gly Lys Ala Pro
                405                 410                 415

Lys Leu Leu Ile Phe Trp Ser Pro Trp Leu Tyr Ser Gly Val Pro Ser
            420                 425                 430

Arg Phe Ser Gly Ser Gly Ser Gly Thr Asp Phe Thr Leu Thr Ile Ser
            435                 440                 445

Ser Leu Gln Pro Glu Asp Phe Ala Thr Tyr Tyr Cys Gln Gln Gly Trp
```

```
                        450                 455                 460
Asp Ser Pro Val Thr Phe Gly Gln Gly Thr Lys Val Glu Ile Lys Arg
465                 470                 475                 480

Gly Ser Thr Ser Gly Ser Gly Lys Pro Gly Ser Gly Glu Gly Ser Thr
                485                 490                 495

Lys Gly Glu Val Gln Leu Val Glu Ser Gly Gly Leu Val Gln Pro
                500                 505                 510

Gly Gly Ser Leu Arg Leu Ser Cys Ala Ala Ser Gly Phe Thr Ile Ser
                515                 520                 525

Asp Phe Gly Ile His Trp Val Arg Gln Ala Pro Gly Lys Gly Leu Glu
                530                 535                 540

Trp Val Ala Ser Ile Trp Pro Ser Gly Gly Tyr Thr Tyr Tyr Ala Asp
545                 550                 555                 560

Ser Val Lys Gly Arg Phe Thr Ile Ser Ala Asp Thr Ser Lys Asn Thr
                565                 570                 575

Ala Tyr Leu Gln Met Asn Ser Leu Arg Ala Glu Asp Thr Ala Val Tyr
                580                 585                 590

Tyr Cys Ala Arg Ser Trp Phe Tyr Ser Trp Tyr Asp Tyr Trp Gly Gln
                595                 600                 605

Gly Thr Leu Val Thr Val Ser Ser
        610                 615

<210> SEQ ID NO 13
<211> LENGTH: 599
<212> TYPE: PRT
<213> ORGANISM: Artificial Sequence
<220> FEATURE:
<223> OTHER INFORMATION: Synthetic

<400> SEQUENCE: 13

Ser Tyr Gln Gly Asn Ser Asp Cys Tyr Phe Gly Asn Gly Ser Ala Tyr
1               5                   10                  15

Arg Gly Thr His Ser Leu Thr Glu Ser Gly Ala Ser Cys Leu Pro Trp
                20                  25                  30

Asn Ser Met Ile Leu Ile Gly Lys Val Tyr Thr Ala Gln Asn Pro Ser
            35                  40                  45

Ala Gln Ala Leu Gly Leu Gly Lys His Asn Tyr Cys Arg Asn Pro Asp
        50                  55                  60

Gly Asp Ala Lys Pro Trp Cys His Val Leu Lys Asn Arg Arg Leu Thr
65                  70                  75                  80

Trp Glu Tyr Cys Asp Val Pro Ser Cys Ser Thr Cys Gly Leu Arg Gln
                85                  90                  95

Tyr Ser Gln Pro Gln Phe Arg Ile Lys Gly Gly Leu Phe Ala Asp Ile
                100                 105                 110

Ala Ser His Pro Trp Gln Ala Ala Ile Phe Ala Lys His Arg Arg Ser
            115                 120                 125

Pro Gly Glu Arg Phe Leu Cys Gly Gly Ile Leu Ile Ser Ser Cys Trp
        130                 135                 140

Ile Leu Ser Ala Ala His Cys Phe Gln Glu Arg Phe Pro Pro His His
145                 150                 155                 160

Leu Thr Val Ile Leu Gly Arg Thr Tyr Arg Val Val Pro Gly Glu Glu
                165                 170                 175

Glu Gln Lys Phe Glu Val Glu Lys Tyr Ile Val His Lys Glu Phe Asp
                180                 185                 190

Asp Asp Thr Tyr Asp Asn Asp Ile Ala Leu Leu Gln Leu Lys Ser Asp
```

```
            195                 200                 205
Ser Ser Arg Cys Ala Gln Glu Ser Val Val Arg Thr Val Cys Leu
    210                 215                 220

Pro Pro Ala Asp Leu Gln Leu Pro Asp Trp Thr Glu Cys Glu Leu Ser
225                 230                 235                 240

Gly Tyr Gly Lys His Glu Ala Leu Ser Pro Phe Tyr Ser Glu Arg Leu
                245                 250                 255

Lys Glu Ala His Val Arg Leu Tyr Pro Ser Ser Arg Cys Thr Ser Gln
                260                 265                 270

His Leu Leu Asn Arg Thr Val Thr Asp Asn Met Leu Cys Ala Gly Asp
            275                 280                 285

Thr Arg Ser Gly Gly Pro Gln Ala Asn Leu His Asp Ala Cys Gln Gly
290                 295                 300

Asp Ser Gly Gly Pro Leu Val Cys Leu Asn Asp Gly Arg Met Thr Leu
305                 310                 315                 320

Val Gly Ile Ile Ser Trp Gly Leu Gly Cys Gly Gln Lys Asp Val Pro
                325                 330                 335

Gly Val Tyr Thr Lys Val Thr Asn Tyr Leu Asp Trp Ile Arg Asp Asn
                340                 345                 350

Met Arg Pro Ala Ser Gly Gly Ser Pro Cys Pro Ser Cys Pro Ala
                355                 360                 365

Pro Glu Phe Leu Gly Gly Pro Ser Val Phe Leu Phe Pro Pro Lys Pro
370                 375                 380

Lys Asp Thr Leu Met Ile Ser Arg Thr Pro Glu Val Thr Cys Val Val
385                 390                 395                 400

Val Asp Val Ser Gln Glu Asp Pro Glu Val Gln Phe Asn Trp Tyr Val
                405                 410                 415

Asp Gly Val Glu Val His Asn Ala Lys Thr Lys Pro Arg Glu Glu Gln
                420                 425                 430

Phe Asn Ser Thr Tyr Arg Val Val Ser Val Leu Thr Val Leu His Gln
                435                 440                 445

Asp Trp Leu Asn Gly Lys Glu Tyr Lys Cys Lys Val Ser Asn Lys Gly
    450                 455                 460

Leu Pro Ser Ser Ile Glu Lys Thr Ile Ser Lys Ala Lys Gly Gln Pro
465                 470                 475                 480

Arg Glu Pro Gln Val Tyr Thr Leu Pro Pro Ser Gln Glu Glu Met Thr
                485                 490                 495

Lys Asn Gln Val Ser Leu Thr Cys Leu Val Lys Gly Phe Tyr Pro Ser
                500                 505                 510

Asp Ile Ala Val Glu Trp Glu Ser Asn Gly Gln Pro Glu Asn Asn Tyr
            515                 520                 525

Lys Thr Thr Pro Pro Val Leu Asp Ser Asp Gly Ser Phe Phe Leu Tyr
    530                 535                 540

Ser Arg Leu Thr Val Asp Lys Ser Arg Trp Gln Glu Gly Asn Val Phe
545                 550                 555                 560

Ser Cys Ser Val Met His Glu Ala Leu His Asn His Tyr Thr Gln Lys
                565                 570                 575

Ser Leu Ser Leu Ser Leu Gly Lys Gly Gly Gly Gly Ser Gly Gly Gly
            580                 585                 590

Gly Ser Gly Gly Gly Gly Ser
            595
```

<210> SEQ ID NO 14

<211> LENGTH: 617
<212> TYPE: PRT
<213> ORGANISM: Artificial Sequence
<220> FEATURE:
<223> OTHER INFORMATION: Synthetic

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Asn Asn
            20                  25                  30

Val Ala Trp Tyr Gln Gln Lys Pro Gly Lys Ala Pro Lys Leu Leu Ile
        35                  40                  45

Phe Trp Ser Pro Trp Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Trp Asp Ser Pro Val
                85                  90                  95

Thr Phe Gly Gln Gly Thr Lys Val Glu Ile Lys Arg Gly Ser Thr Ser
            100                 105                 110

Gly Ser Gly Lys Pro Gly Ser Gly Glu Gly Ser Thr Lys Gly Glu Val
        115                 120                 125

Gln Leu Val Glu Ser Gly Gly Gly Leu Val Gln Pro Gly Gly Ser Leu
    130                 135                 140

Arg Leu Ser Cys Ala Ala Ser Gly Phe Thr Ile Ser Asp Phe Gly Ile
145                 150                 155                 160

His Trp Val Arg Gln Ala Pro Gly Lys Gly Leu Glu Trp Val Ala Ser
                165                 170                 175

Ile Trp Pro Ser Gly Gly Tyr Thr Tyr Tyr Ala Asp Ser Val Lys Gly
            180                 185                 190

Arg Phe Thr Ile Ser Ala Asp Thr Ser Lys Asn Thr Ala Tyr Leu Gln
        195                 200                 205

Met Asn Ser Leu Arg Ala Glu Asp Thr Ala Val Tyr Tyr Cys Ala Arg
    210                 215                 220

Ser Trp Phe Tyr Ser Trp Tyr Asp Tyr Trp Gly Gln Gly Thr Leu Val
225                 230                 235                 240

Thr Val Ser Ser Ala Ser Gly Gly Gly Gly Ser Gly Gly Gly Gly Ser
                245                 250                 255

Gly Gly Gly Gly Ser Ser Tyr Gln Gly Asn Ser Asp Cys Tyr Phe Gly
            260                 265                 270

Asn Gly Ser Ala Tyr Arg Gly Thr His Ser Leu Thr Glu Ser Gly Ala
        275                 280                 285

Ser Cys Leu Pro Trp Asn Ser Met Ile Leu Ile Gly Lys Val Tyr Thr
    290                 295                 300

Ala Gln Asn Pro Ser Ala Gln Ala Leu Gly Leu Gly Lys His Asn Tyr
305                 310                 315                 320

Cys Arg Asn Pro Asp Gly Asp Ala Lys Pro Trp Cys His Val Leu Lys
                325                 330                 335

Asn Arg Arg Leu Thr Trp Glu Tyr Cys Asp Val Pro Ser Cys Ser Thr
            340                 345                 350

Cys Gly Leu Arg Gln Tyr Ser Gln Pro Gln Phe Arg Ile Lys Gly Gly
        355                 360                 365

Leu Phe Ala Asp Ile Ala Ser His Pro Trp Gln Ala Ala Ile Phe Ala
    370                 375                 380

Lys His Arg Arg Ser Pro Gly Glu Arg Phe Leu Cys Gly Gly Ile Leu
385                 390                 395                 400

Ile Ser Ser Cys Trp Ile Leu Ser Ala Ala His Cys Phe Gln Glu Arg
            405                 410                 415

Phe Pro Pro His His Leu Thr Val Ile Leu Gly Arg Thr Tyr Arg Val
        420                 425                 430

Val Pro Gly Glu Glu Glu Gln Lys Phe Glu Val Glu Lys Tyr Ile Val
        435                 440                 445

His Lys Glu Phe Asp Asp Thr Tyr Asp Asn Asp Ile Ala Leu Leu
    450                 455                 460

Gln Leu Lys Ser Asp Ser Ser Arg Cys Ala Gln Glu Ser Ser Val Val
465                 470                 475                 480

Arg Thr Val Cys Leu Pro Pro Ala Asp Leu Gln Leu Pro Asp Trp Thr
            485                 490                 495

Glu Cys Glu Leu Ser Gly Tyr Gly Lys His Glu Ala Leu Ser Pro Phe
        500                 505                 510

Tyr Ser Glu Arg Leu Lys Glu Ala His Val Arg Leu Tyr Pro Ser Ser
    515                 520                 525

Arg Cys Thr Ser Gln His Leu Leu Asn Arg Thr Val Thr Asp Asn Met
530                 535                 540

Leu Cys Ala Gly Asp Thr Arg Ser Gly Gly Pro Gln Ala Asn Leu His
545                 550                 555                 560

Asp Ala Cys Gln Gly Asp Ser Gly Gly Pro Leu Val Cys Leu Asn Asp
            565                 570                 575

Gly Arg Met Thr Leu Val Gly Ile Ile Ser Trp Gly Leu Gly Cys Gly
        580                 585                 590

Gln Lys Asp Val Pro Gly Val Tyr Thr Lys Val Thr Asn Tyr Leu Asp
    595                 600                 605

Trp Ile Arg Asp Asn Met Arg Pro Ala
    610                 615

<210> SEQ ID NO 15
<211> LENGTH: 15
<212> TYPE: PRT
<213> ORGANISM: Artificial Sequence
<220> FEATURE:
<223> OTHER INFORMATION: Synthetic

<400> SEQUENCE: 15

Gly Gly Gly Gly Ser Gly Gly Gly Gly Ser Gly Gly Gly Gly Ser
1               5                   10                  15

<210> SEQ ID NO 16
<211> LENGTH: 18
<212> TYPE: PRT
<213> ORGANISM: Artificial Sequence
<220> FEATURE:
<223> OTHER INFORMATION: Synthetic

<400> SEQUENCE: 16

Gly Ser Thr Ser Gly Ser Gly Lys Pro Gly Ser Gly Glu Gly Ser Thr
1               5                   10                  15

Lys Gly

<210> SEQ ID NO 17
<211> LENGTH: 108
<212> TYPE: PRT
<213> ORGANISM: Artificial Sequence
<220> FEATURE:
<223> OTHER INFORMATION: Synthetic

<400> SEQUENCE: 17

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Gly Trp
            20                  25                  30

Val Ala Trp Tyr Gln Gln Lys Pro Gly Lys Ala Pro Lys Leu Leu Ile
        35                  40                  45

Ser Ser Thr Gly Ser Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Phe Pro Ile
                85                  90                  95

Thr Phe Gly Gln Gly Thr Lys Val Glu Ile Lys Arg
            100                 105
```

<210> SEQ ID NO 18
<211> LENGTH: 120
<212> TYPE: PRT
<213> ORGANISM: Artificial Sequence
<220> FEATURE:
<223> OTHER INFORMATION: Synthetic

<400> SEQUENCE: 18

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Gly Asn Ser
            20                  25                  30

Ser Ile His Trp Val Arg Gln Ala Pro Gly Lys Gly Leu Glu Trp Val
        35                  40                  45

Ala Gly Ile Trp Pro Tyr Trp Gly Ser Thr Tyr Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe Gly Ile Asn Asn Asp Gly Phe Met Asp Tyr Trp Gly Gln
            100                 105                 110

Gly Thr Leu Val Thr Val Ser Ser
        115                 120
```

<210> SEQ ID NO 19
<211> LENGTH: 108
<212> TYPE: PRT
<213> ORGANISM: Artificial Sequence
<220> FEATURE:
<223> OTHER INFORMATION: Synthetic

<400> SEQUENCE: 19

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asp Asn Ser
            20                  25                  30

Val Ala Trp Tyr Gln Gln Lys Pro Gly Lys Ala Pro Lys Leu Leu Ile
        35                  40                  45
```

Ser Ser Ala Arg Ser Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asn Tyr Pro Ile
                85                  90                  95

Thr Phe Gly Gln Gly Thr Lys Val Glu Ile Lys Arg
            100                 105

<210> SEQ ID NO 20
<211> LENGTH: 125
<212> TYPE: PRT
<213> ORGANISM: Artificial Sequence
<220> FEATURE:
<223> OTHER INFORMATION: Synthetic

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Asn Asn Tyr
                20                  25                  30

Gly Ile His Trp Val Arg Gln Ala Pro Gly Lys Gly Leu Glu Trp Val
            35                  40                  45

Ala Gly Ile Trp Pro Tyr Trp Gly Tyr Thr Tyr Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe Asp Ser Asn Ser Tyr Ser Ser Tyr Ser Asp Gly Phe Met
            100                 105                 110

Asp Tyr Trp Gly Gln Gly Thr Leu Val Thr Val Ser Ser
        115                 120                 125

<210> SEQ ID NO 21
<211> LENGTH: 108
<212> TYPE: PRT
<213> ORGANISM: Artificial Sequence
<220> FEATURE:
<223> OTHER INFORMATION: Synthetic

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Gly Gly Trp
                20                  25                  30

Val Ala Trp Tyr Gln Gln Lys Pro Gly Lys Ala Pro Lys Leu Leu Ile
            35                  40                  45

Ser Ser Pro Arg Ser Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Phe Ser Ser Pro Phe
                85                  90                  95

Thr Phe Gly Gln Gly Thr Lys Val Glu Ile Lys Arg
            100                 105

<210> SEQ ID NO 22

```
<211> LENGTH: 116
<212> TYPE: PRT
<213> ORGANISM: Artificial Sequence
<220> FEATURE:
<223> OTHER INFORMATION: Synthetic

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Asn Asp Trp
            20                  25                  30

Ser Ile His Trp Val Arg Gln Ala Pro Gly Lys Gly Leu Glu Trp Val
        35                  40                  45

Ala Tyr Ile Gly Pro Phe Trp Gly Ser Thr Phe Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Tyr Phe Gly Phe Asp Tyr Trp Gly Gln Gly Thr Leu Val
            100                 105                 110

Thr Val Ser Ser
            115
```